(12) United States Patent
Mendoza

(10) Patent No.: US 11,946,843 B2
(45) Date of Patent: Apr. 2, 2024

(54) SAMPLE FILTRATION DEVICE

(71) Applicant: CanaryQ, Inc., Mountain View, CA (US)

(72) Inventor: Estevan Mendoza, Mountain View, CA (US)

(73) Assignee: SPLITRX LLC, Los Gatos, CA (US)

( * ) Notice: Subject to any disclaimer, the term of this patent is extended or adjusted under 35 U.S.C. 154(b) by 938 days.

(21) Appl. No.: 16/625,799

(22) PCT Filed: Jun. 26, 2018

(86) PCT No.: PCT/US2018/039556
§ 371 (c)(1),
(2) Date: Dec. 23, 2019

(87) PCT Pub. No.: WO2019/005833
PCT Pub. Date: Jan. 3, 2019

(65) Prior Publication Data
US 2020/0124508 A1   Apr. 23, 2020

Related U.S. Application Data

(60) Provisional application No. 62/525,039, filed on Jun. 26, 2017.

(51) Int. Cl.
*G01N 1/40*   (2006.01)
*B01L 3/00*   (2006.01)
*G01N 33/49*   (2006.01)

(52) U.S. Cl.
CPC ............ *G01N 1/4077* (2013.01); *B01L 3/502* (2013.01); *G01N 33/492* (2013.01); *B01L 2200/026* (2013.01); *B01L 2300/0681* (2013.01)

(58) Field of Classification Search
CPC .............. G01N 1/4077; G01N 33/492; G01N 33/54386; G01N 33/558;
(Continued)

(56) References Cited

U.S. PATENT DOCUMENTS 3,939,822 A   2/1976   Markowitz
4,761,230 A   8/1988   Pacheco et al.
(Continued)

FOREIGN PATENT DOCUMENTS

AU   2013204820 A1   5/2013
BE      849898 A   6/1977
(Continued)

OTHER PUBLICATIONS

Kim et al.; Portable vibration-assisted filtration device for on-site isolation of blood cells or pathogenic bacteria from whole human blood; Science Direct; Talanta; vol. 179; pp. 201-212; Mar. 1, 2018; (Abstract Only); 2 pages; Retrieved from the internet: ( https://www.sciencedirect.com/science/article/pii/S0039914017310196) on Mar. 14, 2020.
(Continued)

*Primary Examiner* — Dennis White
(74) *Attorney, Agent, or Firm* — Shay Glenn LLP

(57) ABSTRACT

Sample filtration devices are provided. The devices can comprise a filter membrane positioned between an input and output substrate and joined using an adhesive layer. The filter assembly can be used with various sample collection and dispensing devices, such as a flexible container, a bulb pipette, a micropipette, etc. Applying pressure to the filter assembly, e.g., using a flexible container, a bulb pipette or a micropipette can force the fluid through the filter membrane and onto a test strip or cartridge.

20 Claims, 18 Drawing Sheets

(58) Field of Classification Search
CPC ........ G01N 2001/4088; G01N 35/1065; B01L 3/502; B01L 2200/026; B01L 2300/0681; B01L 2300/042; B01L 2300/046; B01L 2300/123; B01L 2400/0616

See application file for complete search history.

(56) References Cited

U.S. PATENT DOCUMENTS

| | | | |
|---|---|---|---|
| D305,934 S | 2/1990 | Sone | |
| 4,915,847 A | 4/1990 | Dillon et al. | |
| 4,976,851 A | 12/1990 | Tanokura et al. | |
| 5,240,862 A * | 8/1993 | Koenhen | G01N 33/491 210/500.24 |
| 5,308,506 A | 5/1994 | McEwen et al. | |
| D355,973 S | 2/1995 | Tjiri et al. | |
| D403,975 S | 1/1999 | Douglas et al. | |
| 5,979,669 A * | 11/1999 | Kitajima | B01D 61/20 210/488 |
| 6,245,244 B1 | 6/2001 | De Rooij | |
| 6,632,681 B1 | 10/2003 | Chu | |
| 6,659,975 B2 | 12/2003 | Amano et al. | |
| D498,850 S | 11/2004 | Ukon | |
| D566,291 S | 4/2008 | Parunak et al. | |
| 7,745,106 B2 | 6/2010 | Beretta et al. | |
| D642,908 S | 4/2011 | Fine et al. | |
| 8,846,333 B2 | 9/2014 | Karlsson | |
| D745,679 S | 12/2015 | Verri et al. | |
| D771,833 S | 11/2016 | Leaver et al. | |
| D771,834 S | 11/2016 | Leaver et al. | |
| D772,427 S | 11/2016 | Leaver et al. | |
| D867,610 S | 11/2019 | Ohata et al. | |
| D875,271 S | 2/2020 | Ringold et al. | |
| 2001/0012612 A1 | 8/2001 | Petersen et al. | |
| 2002/0058030 A1 | 5/2002 | Monroy et al. | |
| 2010/0256350 A1 | 10/2010 | Rhee et al. | |
| 2011/0266160 A1 | 11/2011 | Campbell et al. | |
| 2011/0268609 A1 | 11/2011 | Reggiani et al. | |
| 2012/0118825 A1* | 5/2012 | Margraf | G01N 33/491 210/645 |
| 2012/0138534 A1* | 6/2012 | Chung | B03C 1/0332 210/695 |
| 2013/0105393 A1 | 5/2013 | Hiesinger et al. | |
| 2014/0080112 A1 | 3/2014 | Ryan et al. | |
| 2014/0329268 A1 | 11/2014 | Karisson | |
| 2015/0060353 A1 | 3/2015 | Neijzen et al. | |
| 2016/0010052 A1 | 1/2016 | Wainwright et al. | |
| 2016/0082174 A1 | 3/2016 | Margraf et al. | |

FOREIGN PATENT DOCUMENTS

| | | |
|---|---|---|
| CN | 1169886 A | 1/1998 |
| CN | 102791616 A | 11/2012 |
| CN | 102803958 A | 11/2012 |
| CN | 103038624 A | 4/2013 |
| CN | 105874052 A | 8/2016 |
| EP | 1383861 A2 | 1/2004 |
| GB | 2232599 A | 12/1990 |
| JP | S5798857 A | 6/1982 |
| JP | 2000074906 A | 3/2000 |
| JP | 2001299730 A | 10/2001 |
| JP | 2004337852 A | 12/2004 |
| JP | 2006118936 A | 5/2006 |
| KR | 3020180009715 | 6/2018 |
| WO | WO2016/073415 A2 | 5/2016 |
| WO | WO2019/086286 A1 | 5/2019 |

OTHER PUBLICATIONS

Mendoza, Design U.S. Appl. No. 29/674,574 entitled "Blood sample filtration device," filed Dec. 21, 2018.

* cited by examiner

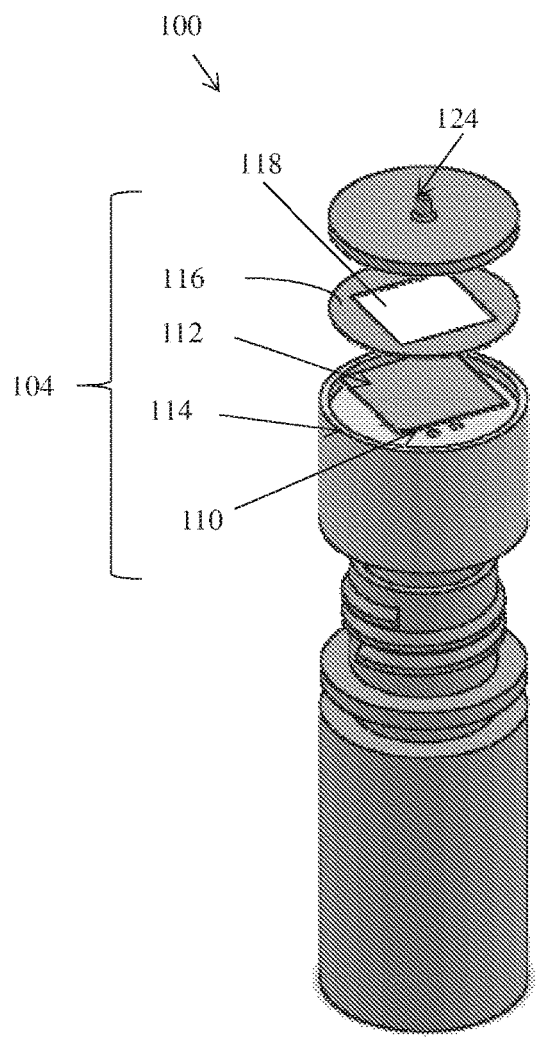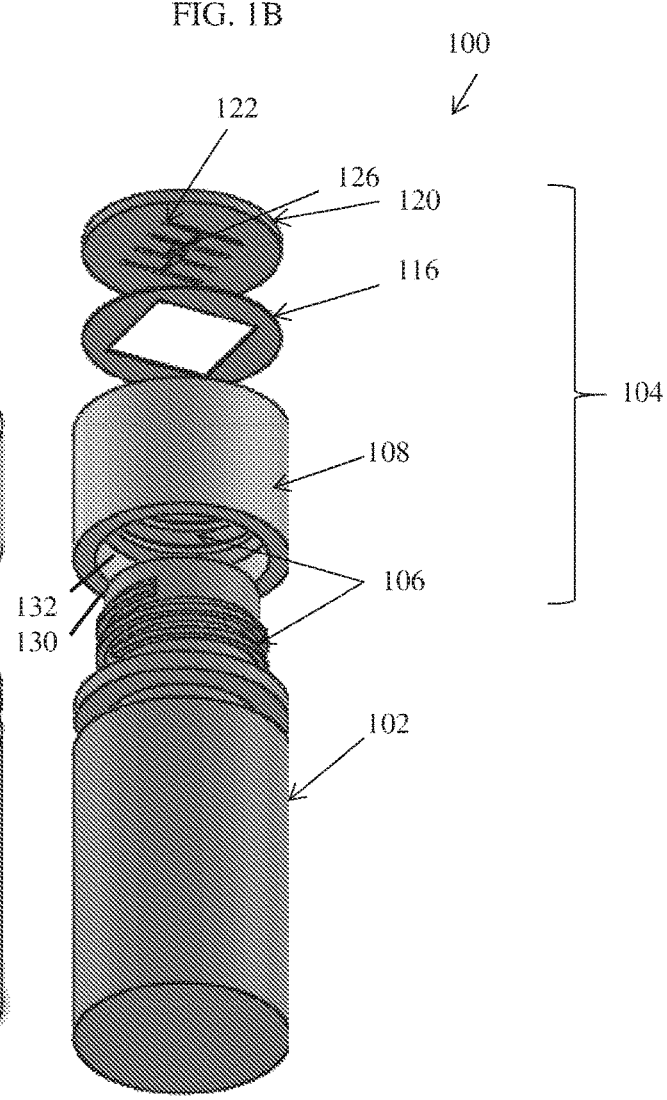

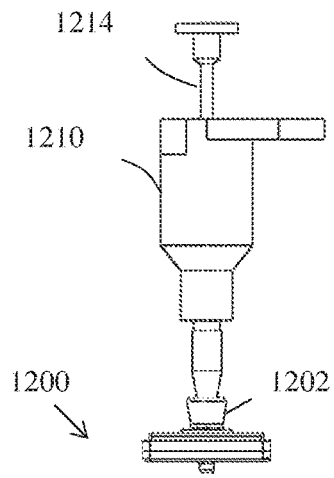
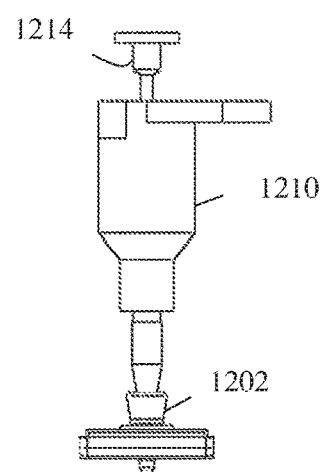
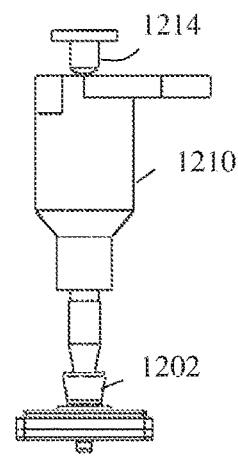
FIG. 12A     FIG. 12B     FIG. 12C
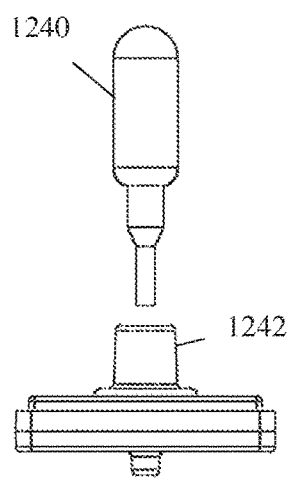
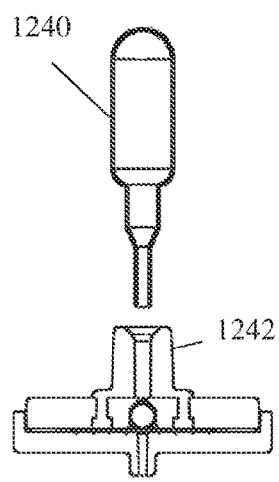
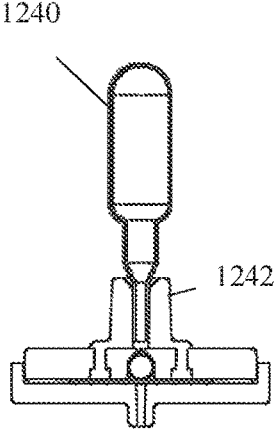
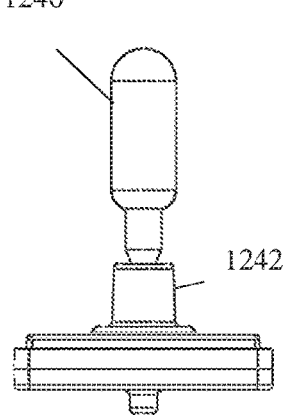
FIG. 12D     FIG. 12E     FIG. 12F     FIG. 12G

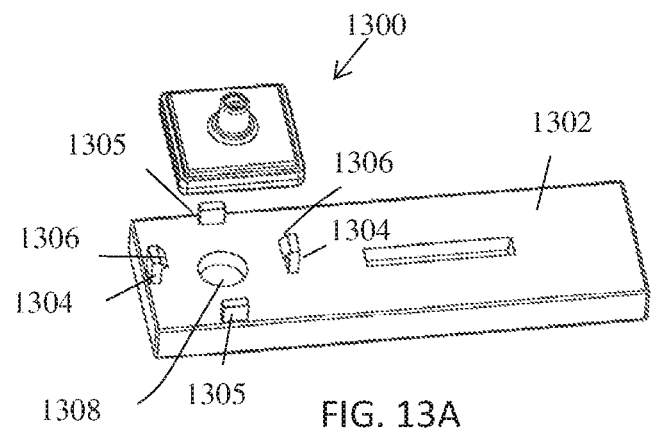
FIG. 13A
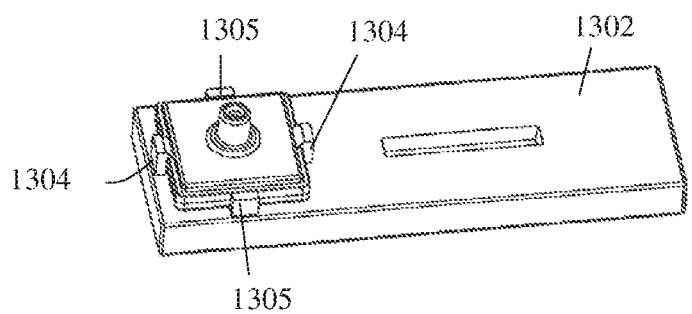
FIG. 13B
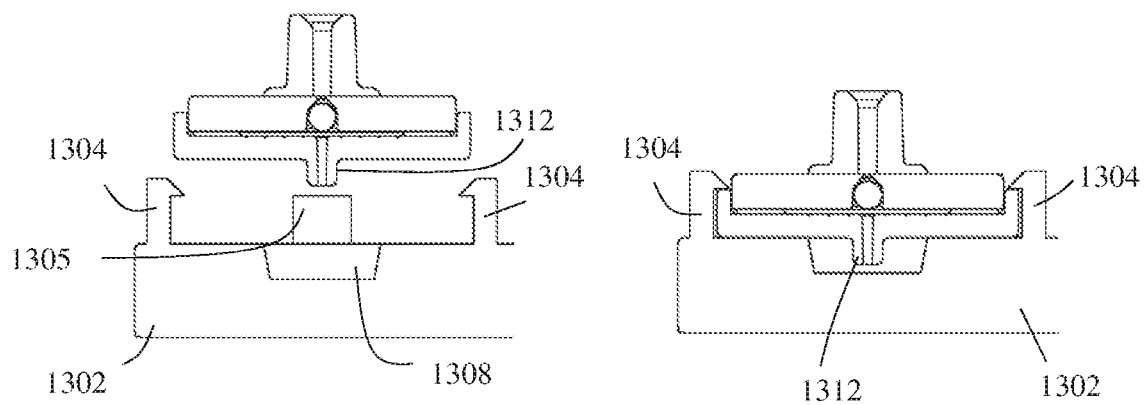
FIG. 13C
FIG. 13D

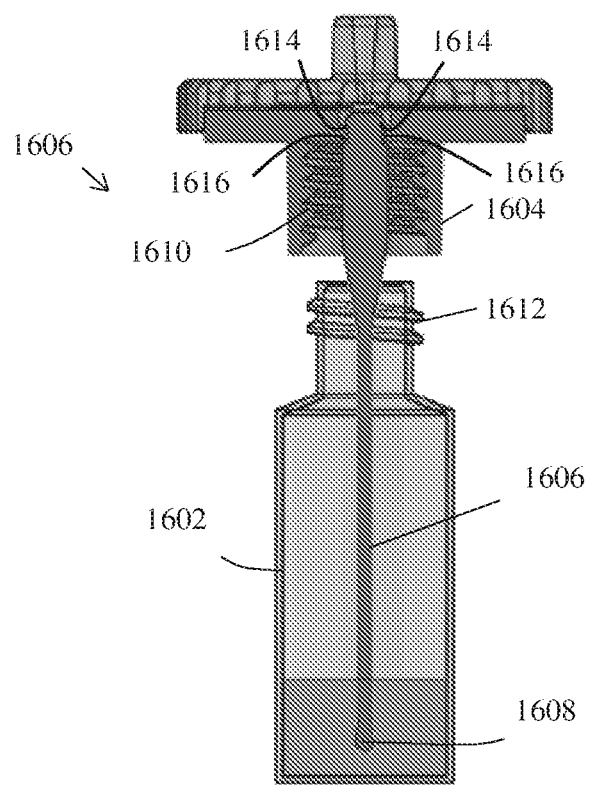
FIG. 16A
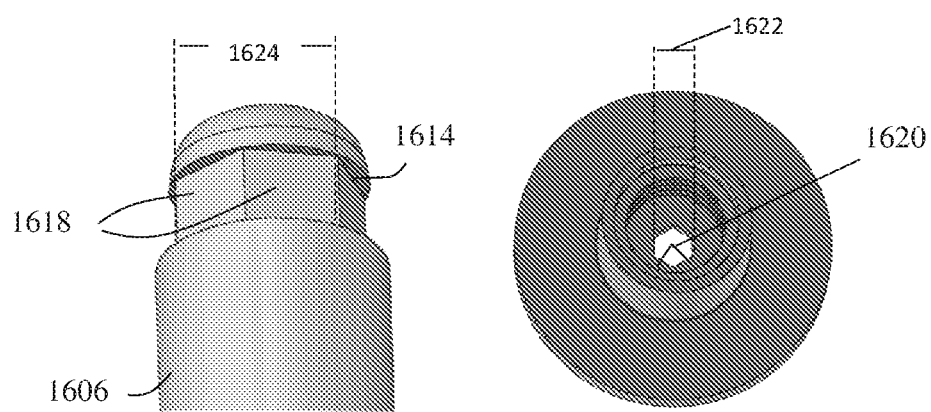
FIG. 16B
FIG. 16C

SAMPLE FILTRATION DEVICE

CROSS REFERENCE TO EARLIER APPLICATIONS

This application claims the benefit of U.S. Provisional Patent Application No. 62/525,039 filed Jun. 26, 2017, the entire disclosure of which is hereby incorporated by reference herein.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This application relates to the field of filters for sample processing.

BACKGROUND

Sample processing is a complicated process as it is typically performed by trained professionals with specialized equipment to carry out all of the steps required to prepare a sample. Generally, sample processing for a lateral flow immunoassay comprises collecting a specific volume of blood; mixing the volume with the running buffer solution, separating cells from buffer and plasma, and delivering a specific volume of diluted plasma to the test strip or device. A typical protocol for accomplishing these tasks includes using a precision pipette to collect a sample of blood from a vacutainer tube via venipuncture and depositing the sample into a centrifuge tube. A specific amount of buffer solution is then pipetted into the centrifuge tube with the blood sample. The mixture is then drawn into the pipette several times until it is homogeneous. The mixture is then centrifuged for a specified amount of time at high rotational speed. For example, the Eppendorf MiniSpin can rotate at 8000 rpm for 60 sec to separate 500 uL of whole blood. A specific amount of the supernatant is then pipetted onto the test strip.

As made clear by the above procedure, sample processing is currently a time consuming process requiring trained professionals and expensive equipment to ready a sample. A need exists for a simpler process that allows lay people to perform sample processing at home and in the field.

SUMMARY OF THE DISCLOSURE

In one aspect, embodiments of a sample filtration device for processing a sample are provided. The device comprises a flexible container; a cap configured to seal to the flexible container, the cap comprising one or more inlet holes in fluid communication with the flexible container; an asymmetric filter in fluid communication with the one or more inlet holes and configured to filter the sample into a filtrate; a support component comprising one or more channels in fluid communication with the filtrate from the asymmetric filter; an adhesive layer configured to join the filter to the cap or the support component; and an outlet in fluid communication with the one or more channels.

In some embodiments, the adhesive layer is a double sided adhesive layer. The cap can seal to the flexible container via a threaded connection. In some embodiments, the sample fluid comprises whole blood. The adhesive layer can comprise a cutout portion configured to expose the asymmetric filter when the adhesive layer is adhered to the asymmetric filter. In some embodiments, the one or more channels comprises a serpentine channel or a plurality of channels. The outlet can comprise a spout. In some embodiments, the cap comprises at least one of polypropylene, polycarbonate, aluminum, and steel. A surface of the cap that joins the adhesive layer can be substantially flat. In some embodiments, a surface of the cap that joins the adhesive layer comprises proud features. A surface of the support component that joins the adhesive layer can be substantially flat. In some embodiments, a surface of the support component that joins the adhesive layer comprises proud features. The adhesive layer can comprise a silicone or acrylic based adhesive. In some embodiments, a width of the filter membrane is about 15 mm. The length of the filter membrane can be about 15 mm. In some embodiments, the asymmetric filter comprises a pore size of about 0.8 µm. The filter membrane can comprise at least one of polycarbonate, polysulfone, polyester, polyethylene, and polypropylene. In some embodiments, the cap comprises a ridge around its perimeter. The support component can be sized to fit inside the ridge of the cap. In some embodiments, the support component comprises a ridge around its perimeter. The cap can be sized to fit inside the ridge of the support component. In some embodiments, the one or more channels extend throughout an area of the filter membrane. The one or more channels can comprise a spacing of about 1.5 mm between channels. In some embodiments, a configuration of the channels is selected based on a material and roughness of a surface of the support component. The sealing portion of the cap can be smaller than a perimeter of the cap to accommodate a filter size greater than a size of an opening of the container. In some embodiments, the device comprises a swab connected to the cap and extending throughout a length of the flexible container. An end of the swab can comprise an undercut configured to mate with a cutout portion of the cap. In some embodiments, the device comprises a fluid path through the cutout around the swab when the cap is attached to the swab. The adhesive layer can be configured to join the filter to the cap. The adhesive layer can be configured to join the filter to the support component.

In another aspect, embodiments of a method of filtering a sample are provided. The method comprises providing a sample filtration device comprising a flexible container and a cap configured to seal to the flexible container; placing a sample fluid into the flexible container; squeezing the flexible container, thereby pushing the sample fluid through one or more inlet holes in the cap, through an asymmetric filter to create a filtrate, and pushing the filtrate through one or more channels to an outlet.

In some embodiments, the method comprises squeezing the flexible container. The sample fluid can comprise whole blood. In some embodiments, the method comprises adding a buffer solution to the flexible container. The method can comprise mixing the sample fluid before squeezing the flexible container. In some embodiments, the method comprises inverting the flexible container before squeezing the flexible container. Squeezing the container can generate a pressure of about 0.25-5 psi. In some embodiments, the method comprises using the filtrate in a testing or diagnostic apparatus. The method can comprise using the filtrate in a lateral flow immunoassay (LFIA) test. In some embodiments, the method comprises using the filtrate to test for blood alcohol content, cannabinoid detection, or a vitamin deficiency. The method can comprise using the filtrate to isolate cell free DNA that circulates in the blood stream. In some embodiments, the method comprises using the filtrate on a lateral flow immunoassay test strip.

In another aspect, embodiments of methods of manufacturing a sample filtration device are provided. The method comprises providing a first substrate comprising an inlet hole; providing an asymmetric filter in fluid communication with the inlet hole and configured to filter the sample into a filtrate; providing a second substrate comprising one or more channels in fluid communication with the filtrate from the filter and in fluid communication with an outlet hole; and providing an adhesive layer comprising a central cutout smaller than a size of the asymmetric filter, the adhesive layer configured to join the asymmetric filter to the first substrate or the second substrate.

In some embodiments, the method comprises compressing the filter assembly together to ensure the adhesive layer binds to adjacent surfaces and seals a perimeter of the filter membrane. The first substrate can be a cap. In some embodiments, the method comprises attaching a flexible connector to the first substrate or the second substrate. Attaching the flexible connector can comprise overmolding the flexible connector onto the first substrate. In some embodiments, the method comprises attaching the flexible connector comprises using mechanical interlocks to attach the flexible connector to the first substrate. The flexible connector can comprise a funnel shaped inlet leading to a tube portion, the tube portion in fluid communication with a contracting hole with a diameter smaller than the diameter of the tube portion, wherein the contracting hole is in fluid communication with the inlet hole of the first substrate. In some embodiments, the method comprises providing a ball valve in a cavity near the inlet hole, the ball valve configured to reversibly seal the inlet hole. The method can comprise adhering the asymmetric filter to the first substrate using the adhesive layer. In some embodiments, the method comprises adhering the asymmetric filter to the second substrate using the adhesive layer. The method can comprise forming a ridge around at least a portion of the second substrate. In some embodiments, first substrate is shaped to fit within the ridge. The method can comprise forming a ridge around at least a portion of the first substrate. forming a ridge around at least a portion of the first substrate. In some embodiments, the second substrate is shaped to fit within the ridge.

In another aspect, a sample filtration device is provided. The device comprises a flexible connector comprising a funnel shaped opening leading to a tube portion; an input substrate comprising an inlet contracting hole in fluid connection with the tube portion; an asymmetric filter membrane in fluid communication with the inlet contracting hole and configured to filter the sample into a filtrate; an adhesive layer configured to join to the asymmetric filter membrane, the adhesive layer comprising a central cutout configured to expose a central portion of the filter membrane; and an output substrate comprising one or more channels in fluid communication with the filtrate from the asymmetric filter, the one or more channels in fluid communication with an outlet of the output substrate.

In some embodiments, the sample filtration device comprises a ball valve configured to reversibly seal the inlet contracting hole. The ball can be positioned in the cavity between the inlet contracting hole and the filter membrane. In some embodiments, the ball valve is configured to prevent back flow caused by release of activation action. The ball can comprise at least one of a rubber, plastic, ceramic, and metal. In some embodiments, the material of the ball is selected based on an intended orientation of use of the filter assembly. A low density material can be selected for an upright orientation. A high density material can be selected for an upside down orientation. In some embodiments, the flexible connector opening and tube portion are shaped to receive a micropipette tip. An external surface of the flexible connector can be shaped to mate with and seal to an inner surface of an opening of a squeeze bottle. In some embodiments, the funnel shaped opening comprises a length of about 1 mm. The funnel shaped opening can comprise an angle of about 45°. In some embodiments, the tube portion comprises a length of about 7 mm. The tube portion can comprise a minimum inner diameter of about 1.5 mm. In some embodiments, the contracting hole has a diameter of about 0.75 mm. The filter membrane can be adhered to the input substrate. In some embodiments, the filter membrane is adhered to the output substrate. The flexible connector can comprise at least one of TPE, silicone, rubbers, polyurethane, LDPE, HDPE, PP, and plasticized PVC. In some embodiments, a wall thickness of the flexible connector is about 2 mm. The adhesive layer can be a double sided adhesive layer. In some embodiments, the sample fluid comprises whole blood. A size of the asymmetric filter can be smaller than a size of the adhesive layer outer perimeter. In some embodiments, the one or more channels comprises a serpentine channel or a plurality of channels. The outlet can comprise a spout. In some embodiments, a surface of at least one of the input substrate and output substrate adjacent to the filter membrane is flat. A surface of at least one of the input substrate and the output substrate adjacent to the filter membrane can comprise proud features. In some embodiments, the adhesive layer comprises a silicone or acrylic based adhesive. A width of the filter membrane can be about 15 mm. In some embodiments, a length of the filter membrane is about 15 mm. The asymmetric filter can comprise a pore size of about 0.8 µm. In some embodiments, the filter membrane comprises at least one of polycarbonate, polysulfone, polyester, polyethylene, and polypropylene. The output substrate can comprise a ridge around its perimeter. In some embodiments, the input substrate is sized to fit inside the ridge of the output substrate. The input substrate can comprise a ridge around its perimeter. In some embodiments, the output substrate is sized to fit inside a ridge of the input substrate. The one or more channels an extend throughout an area of the filter membrane. In some embodiments, the one or more channels comprise a spacing of about 1.5 mm between channels. A configuration of the channels can be selected based on a material and roughness of a surface of the support component. In some embodiments, a diameter of the inlet contracting hole is less than a diameter of the tube portion. The flexible connector can be connected to the input substrate using mechanical interlocks. In some embodiments, a diagnostic system comprising the sample filtration device and a test cartridge is provided. The test cartridge comprises aligning features configured to align the outlet of the sample filtration device with a sample input area of the test cartridge. The cartridge can comprise latches configured to secure the sample filtration device to the test cartridge. In some embodiments, the aligning features are the latches. The output substrate can comprise adhesive configured to adhere the sample filtration device to a test cartridge. In some embodiments, the output substrate comprises a bonding agent configured to adhere the sample filtration device to a test cartridge. A top portion of the tube portion can comprise an undercut configured to mate with a barb. In some embodiments, an array comprising a plurality of the sample filtration devices is provided. The array can comprise 2, 3, 4, 6, 8, or 12 sample filtration devices.

In yet another aspect, a method of filtering a sample is provided. The method comprises providing a sample filtration device comprising a flexible connector comprising a funnel shaped opening leading to a tube portion; the tube portion in fluid communication with an inlet of an input substrate, the inlet in fluid communication with an asymmetric filter membrane, the asymmetric filter membrane connected to an adhesive layer, and an output substrate comprising one or more channels configured to receive filtrate from the filter membrane and comprising an outlet; attaching a sample collection or dispensing device to the flexible container; and applying pressure to the sample collection or dispensing device, thereby pushing the sample fluid through the asymmetric filter to create a filtrate, and pushing the filtrate through one or more channels to the outlet.

In some embodiments, attaching the sample collection or dispensing device comprises inserting a micropipette tip into the funnel shaped opening. Attaching the sample collection or dispensing device can comprise inserting the flexible connector into an opening of a flexible container. In some embodiments, the method comprises adding buffer solution to the flexible container. The method can comprise squeezing the flexible container to dispense the filtrate on a test strip or cartridge. In some embodiments, the method comprises inverting the flexible container before squeezing the flexible container. Squeezing the container can generate a pressure of 0.25-5 psi. In some embodiments, attaching the sample collection or dispensing device comprises inserting a barb into the funnel shaped opening. Attaching the sample collection or dispensing device can comprise inserting a male connector into the funnel shaped opening. In some embodiments, the method comprises dispensing the filtrate onto a test strip. The sample fluid can comprise whole blood. In some embodiments, the sample fluid comprises diluted blood. The method can comprise adding a buffer solution to the sample collection or dispensing device. In some embodiments, the method comprises mixing the sample fluid and the buffer solution. The method can comprise using the filtrate in a testing or diagnostic apparatus. The method can comprise using the filtrate in a lateral flow immunoassay (LFIA) test. In some embodiments, the method comprises using the filtrate to test for blood alcohol content, a vitamin deficiency, or cannabinoid detection. The method can comprise using the filtrate to isolate cell free DNA that circulates in the blood stream. In some embodiments, the method comprises using the filtrate on a lateral flow immunoassay test strip. The method can comprise placing the sample filtration device on a test cartridge. In some embodiments, placing the sample filtration device on the test cartridge comprises latching the sample filtration device to the test cartridge. Placing the sample filtration device on the test cartridge can comprise adhering the sample filtration device to the test cartridge. In some embodiments, placing the sample filtration device on the test cartridge comprises bonding the sample filtration device to the test cartridge.

In another aspect, a sample filtration device is provided. The device comprises an input substrate comprising an inlet hole; an asymmetric filter membrane in fluid communication with the inlet hole and configured to filter the sample into a filtrate; an adhesive layer configured to join to the asymmetric filter membrane, the adhesive layer comprising a central cutout configured to expose a central portion of the filter membrane; and an output substrate comprising one or more channels in fluid communication with the filtrate from the asymmetric filter, the one or more channels in fluid communication with an outlet of the output substrate.

In some embodiments, the device comprises a flexible connector attached to the inlet hole, the flexible connector comprising a funnel shaped opening in fluid communication with a tube shaped portion, the tube shaped portion in fluid communication with the inlet hole. The flexible connector can be shaped to mate to a flexible container, a bulb pipette, a micropipette, and a barb. In some embodiments, at least one of the input substrate or the output substrate comprises a portion of a cap of a flexible container. The device can comprise a ball valve configured to reversibly seal the inlet hole. In some embodiments, the ball is positioned in the cavity between the inlet hole and the filter membrane. The ball valve can be configured to prevent back flow caused by release of activation action. In some embodiments, the ball comprises at least one of a rubber, plastic, ceramic, and metal. The material of the ball can be selected based on an intended orientation of use of the filter assembly. In some embodiments, a low density material is selected for an upright orientation. In some embodiments, a high density material is selected for an upside down orientation. The filter membrane can be adhered to the input substrate. In some embodiments, the filter membrane is adhered to the output substrate. The adhesive layer can be a double sided adhesive layer. In some embodiments, the sample fluid comprises whole blood. In some embodiments, a size of the asymmetric filter is smaller than a size of the adhesive layer outer perimeter. The one or more channels can comprise a serpentine channel or a plurality of channels. In some embodiments, the outlet comprises a spout. A surface of at least one of the input substrate and output substrate adjacent to the filter membrane can be substantially flat. In some embodiments, a surface of at least one of the input substrate and output substrate adjacent to the filter membrane comprises proud features. The adhesive layer can comprise a silicone or acrylic based adhesive. A width and/or length of the filter membrane can be about 15-17 mm. In some embodiments, the asymmetric filter comprises a pore size of about 0.8 µm. The filter membrane can comprise at least one of polycarbonate, polysulfone, polyester, polyethylene, and polypropylene. In some embodiments, the output substrate comprises a ridge around its perimeter. The input substrate can be sized to fit inside the ridge of the output substrate. In some embodiments, the input substrate comprises a ridge around its perimeter. The output substrate can be sized to fit inside a ridge of the input substrate. In some embodiments, the one or more channels extend throughout an area of the filter membrane. The one or more channels can comprise a spacing of about 1.5 mm between channels. In some embodiments, a configuration of the channels is selected based on a material and roughness of a surface of the support component. At least one of the input substrate and the output substrate comprises a rigid material. The device can comprise a connector configured to attach the device to a sample collection and dispensing device.

In another aspect, a method of filtering a sample is provided. The method comprises providing a sample filtration device comprising an input substrate comprising an inlet hole; an asymmetric filter membrane in fluid communication with the inlet hole and configured to filter the sample into a filtrate; an adhesive layer configured to join to the asymmetric filter membrane, the adhesive layer comprising a central cutout configured to expose a central portion of the filter membrane; and an output substrate comprising one or more channels in fluid communication with the filtrate from the asymmetric filter, the one or more channels in fluid communication with an outlet of the output substrate; connecting a sample collecting or dispensing device to the inlet hole; and activating the sample collecting or dispensing device to drive the sample through the filter membrane.

In some embodiments, the method comprises connecting a flexible connector to the filtration device, the flexible connector in fluid communication with the inlet hole. Connecting the sample collection or dispensing device can comprise fluidly connecting a micropipette tip to the inlet hole. In some embodiments, connecting the sample collection or dispensing device comprises fluidly connecting a flexible connector to the inlet hole. The method can comprise activating the sample collection or dispensing device to drive the sample through the filter membrane. In some embodiments, the method comprises dispensing the filtrate onto a test strip. The sample fluid can comprise whole or diluted blood. The method can comprise adding a buffer solution to the sample collection or dispensing device. In some embodiments, the method comprises mixing the sample fluid and the buffer solution. The method can comprise using the filtrate in a testing or diagnostic apparatus. In some embodiments, the method comprises using the filtrate in a lateral flow immunoassay (LFIA) test. The method can comprise using the filtrate to test for blood alcohol content, a vitamin deficiency, or cannabinoid detection. In some embodiments, the method comprises using the filtrate to isolate cell free DNA that circulates in the blood stream. The method can comprise using the filtrate on a lateral flow immunoassay test strip. In some embodiments, the method comprises placing the sample filtration device on a test cartridge. The method can comprise placing the sample filtration device on the test cartridge comprises latching the sample filtration device to the test cartridge.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B illustrate various views of an embodiment of a sample filtration device.

FIGS. 12A-12G show an embodiment of a micropipette inserted into a sample filtration device and being used to push sample through the device.

FIGS. 13A-13F depicts embodiments of a sample filtration device being used with a test cartridge.

FIGS. 16A-C depict an embodiment of a sample filtration device comprising a flexible container and a swab.

DETAILED DESCRIPTION

Figure 2A:
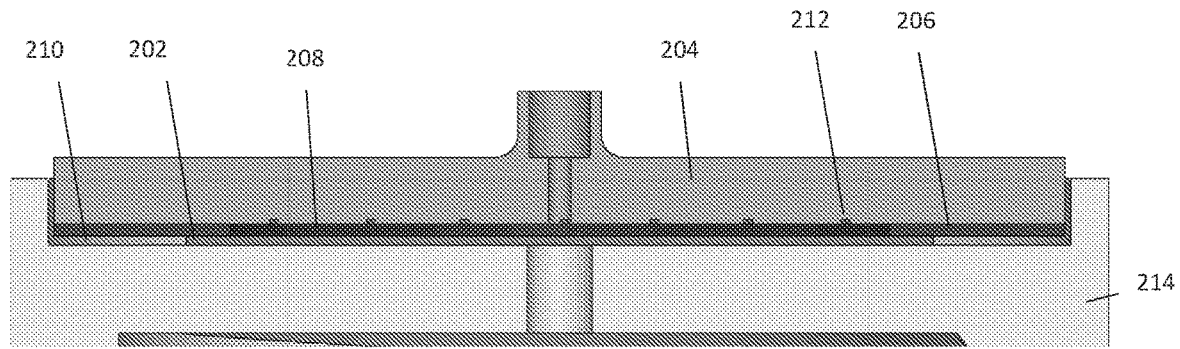
FIGS. 2A-2C show a side view of a portion of an embodiment of a sample filtration device.

Embodiments of sample filtration devices are provided herein. The devices comprise a simple construction, comprising a filter membrane positioned between two substrates and attached to adjacent surfaces and sealed using an adhesive layer (e.g., a double sided adhesive layer). The substrates surrounding the filter membrane can comprise various components. For example, in some embodiments disclosed herein, the substrates comprise portions of a lid that can be used with a flexible container. In other embodiments, the substrates comprise substrates that can be connected to a flexible connector. Throughout the embodiments, the filtering portion of the device comprises a filter membrane joined to a supporting substrate using an adhesive layer with a cutout configured to expose the filter membrane. An output substrate on an opposite side of the filter membrane from the supporting substrate can comprise a single or a plurality of channels configured to receive filtrate produced by the filter membrane. The filtration device can comprise an outlet configured to output the filtrate.

The simple design of the filtering devices can allow for ease of manufacturing as adhering using the adhesive layer can replace typical bonding processes (e.g., liquid adhesive, ultrasonic welding) used in the manufacture of traditional sample filtration devices. Ease of manufacturing can reduce the consumer cost of the filtration product. The filtration devices also provide a very simple sample processing procedure. The simplicity of the process can allow for the near instantaneous capture and processing of samples (e.g., whole blood), a task typically taking days to weeks to achieve a result. The simplicity of the product also allows the processing, which usually occurs in a lab, to be performed in the field and at home. The devices can be used in conjunction with testing and diagnostic devices (e.g., HIV tests, pregnancy test), allowing for fast, at home and in the field sampling, testing, and diagnosis.

FIGS. 1A and 1B illustrate top and bottom perspective views of an embodiment of a sample filtration device 100. The device 100 comprises a flexible container 102 and a cap 104. The flexible container 102 is configured to mate to the cap 104 using threads 106. Other mating mechanisms are also possible (e.g., snap fit, etc.). The flexible container 102 can comprise a cylindrical shape, but other shapes are also possible (e.g., ovular, spherical, square, etc.).

The cap 104 comprises a cap housing 108. The filter mechanism is positioned at a top section of the cap 104. Inlet holes 110 allow sample fluid to enter the filter mechanism from the flexible container. Squeezing the flexible container can create a pressure gradient to urge the sample fluid through the inlet holes 110. Filter membrane 112 is positioned above inlet holes 110. The filter membrane 112 is shown as having a square shape, but other shapes are possible as long as they fit within the footprint of the ridge 114 of the cap housing 108. A double-sided adhesive layer 116 is positioned above the filter membrane 112. The adhesive layer 116 comprises a cut-out portion 118 configured to expose the filter membrane 112 and allow access to the support component 120 comprising mini-channels 122 and outlet 124, positioned above the adhesive layer 116. The mini-channels 122 are positioned on a bottom side of the support component 120, nearest to the filter membrane 112. An exit hole 126 in the channels leads to the outlet 124. As shown in FIG. 1A, the outlet 124 can comprise a spout feature.

When the threads (or other mating mechanism) are engaged, the cap 104 and flexible container 102 form a fluidic seal. The seal is formed at the interference of the perimeter 130 forming the opening of the flexible container and the flat surface 132 of the cap housing. Once sealed, the cap only allows fluid to flow through the inlet hole(s) 110 located on the cap housing 108 and into the filter assembly. In some embodiments, the cap comprises only one opening to function properly, however multiple holes provide redundancy to prevent blockage caused by solids inside of the device. These solids might include clots, particulates, or items left inside the flexible container 102 by the user. The housing 108 also comprises a ridge 114 to facilitate assembly and self-centering. Furthermore, this ridge prevents users from tampering with the device by blocking access to the adhesive once assembled.

The cap 104 can comprise materials that provide sufficient rigidity which include, but are not limited to, thermoplastics like polypropylene or polycarbonate or metals such as aluminum or steel.

The face that interfaces with the filter stack up is substantially flat. That is, it is preferred that there exists no void, or spacing, or features between these faces. A flat design can provide ease in manufacturing. In some embodiments, a void, or spacing, or proud features are placed between these faces. Such features can help to facilitate flow. In such embodiments, care should be taken that the spacing or features do not substantially restrict the lateral flow of the blood and buffer mixture. The reason for this is because after the filter is pressurized, a thin pocket will form as a result of the pressure differential across the filter membrane.

Figure 2B:
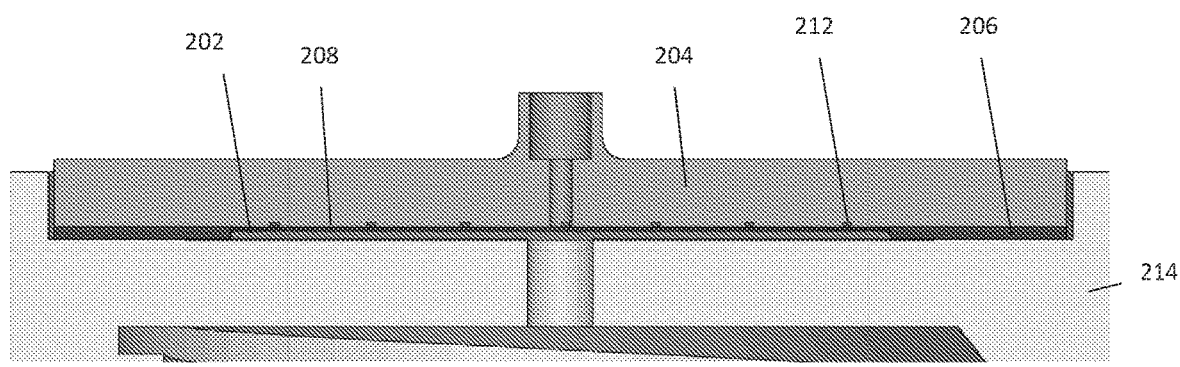
Figure 2C:
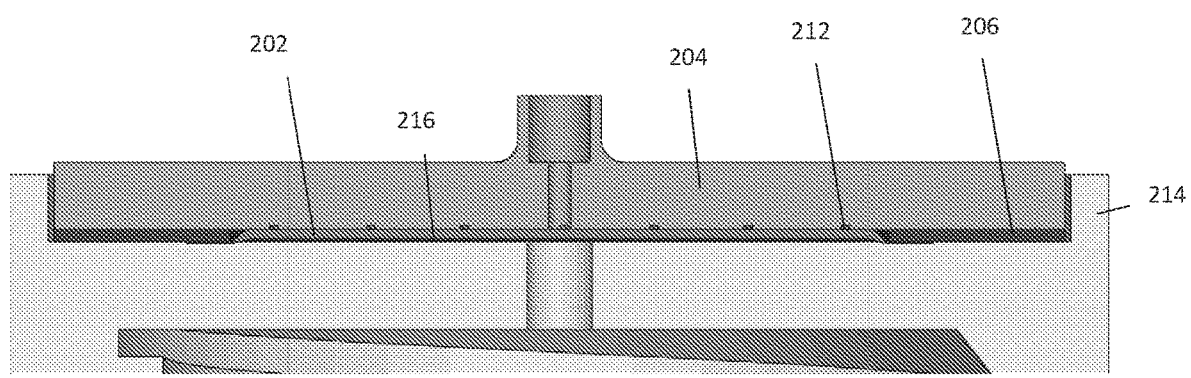

FIGS. 2A-2C illustrate a detailed view of the filter membrane 202, the support component 204, and the double sided adhesive 206. As shown in FIG. 2A, the filter membrane 202 is positioned at the bottom. The double sided adhesive 206 is positioned above the filter membrane 202 and has an opening or cutout 208 in its center. Prior to sealing using the double sided adhesive 206, the assembly comprises a gap 210 between the double sided adhesive 206 and the cap housing 214 and surrounding the filter membrane 202, as shown in FIG. 2A. After sealing, the adhesive 206 seals to the filter membrane 202 and the cap housing 214, eliminating or minimizing gap 210, as shown in FIG. 2B. After pressurization (e.g., squeezing of the flexible container), a thin pocket 216 can form between the filter membrane 202 and the cap housing 214, shown in FIG. 2C.

The double sided adhesive is a pressure sensitive adhesive and is meant to adhere to multiple surfaces when assembled. On one side, it mates only to the support component. On the other side, it mates with both the filter membrane(s) and the cap housing. In some applications, it may be desired to prevent deflection of the filter membrane upon pressurization (without pocket formation) by reversing the order in which the filters and the double sided adhesive are stacked. In this reversed configuration, on one side, the double sided adhesive mates with both the filter membrane and the rigid support component, and on the other side, the double sided adhesive mates with only the cap housing. Because this side mates with multiple surfaces, a double sided adhesive that is thicker than the compressed thickness of the filter membrane should be used to prevent excessive residual stresses on the support structure, which cause unbinding of the double sided adhesive.

The double sided adhesive contains an inner cutout that has a perimeter that is smaller than the filter membrane's perimeter. The outer perimeter of the double sided adhesive preferably has a size that is smaller than the perimeter than the support component's perimeter; however, the double sided adhesive outer perimeter can be the same or larger than the support component and still function properly. The double sided adhesive prevents fluid from bypassing the filter membrane around the perimeter, thereby causing fluid to flow through the membrane, which ensures proper filtration behavior is achieved. The adhesion strength can be sufficient so that when the user operates the device by supplying pressure, the double sided adhesive does not delaminate from any of the surfaces it is adhered to. The thickness of the double sided adhesive should be chosen so that there is sufficient clearance for the filter membrane to allow lateral flow of the unfiltered sample mixture when pressurized. This lateral flow allows the entire filter area to be utilized for filtration. To avoid using excessively thick pressure sensitive adhesives, a substrate polymer film with double sided adhesive on each side can be used to account for the thickness necessary for the device to function. Another technique to account for the necessary thickness is to include a raised surface on the support component that accounts for the necessary thickness required for proper function.

The adhesive can comprise, but is not limited to, silicone or acrylic based adhesives. To ensure that the double sided adhesive properly binds to all necessary surfaces, the assembly can be compressed together. The filter membrane can also compress, remain pinched, and seal at the edges by the adhesive. Other ways to seal the perimeter of the filter membrane include compression by ultrasonic welding. If the filter material is compatible with the cap housing or the support component, then the filter membrane can be directly ultrasonically welded to the surface of the housing or support component. Another technique can use an ultrasonic bond between the support component and the cap housing. This bond can apply a continuous pinching stress to seal the perimeter of the filter membrane. In addition to ultrasonic bonding, the same type of bond can be performed using a liquid adhesive.

The filter membrane is a thin component that is placed in the center of the assembly. The filter membrane can be coated with chemicals or dry reagents. The filter membrane can be cut into virtually any size and shape. It is aligned so that the perimeter of the filter membrane resides outside of the perimeter of the inner cutout of the double sided adhesive to allow for proper sealing. Furthermore, the filter membrane's perimeter should reside within the outer perimeter of the double sided adhesive outer perimeter (shown best in FIG. 2A) to permit the double sided adhesive to properly adhere to the support component.

In some embodiments, the filter can be about 15 mm by about 15 mm. Other dimensions are also possible. For example, the filter can have a length of about 12-18 mm and a width of about 12-18 mm. In some embodiments, the filter has a pore size of about 0.8 µm. Other pore sizes are also possible (e.g., 0.2 m, 0.45 m, 1.0 m, 0.5 m, etc.). In some embodiments, using a 15×15 mm asymmetric filter with a pore size of 0.8 µm can produce enough sample to run a lateral flow immunoassay test at a 1:10 dilution of blood. This concentration can yield about 100 μL or 2-3 drops of processed sample to perform the assay. A typical lateral flow immunoassay test strip can run with about 50 μL or more of processed sample.

The filtration capacity of the filter is directly related to the area of the exposed membrane and concentration of the biological sample mixture. Therefore, a variety of shapes and sizes can be used to accommodate different applications. If the filter membrane is an asymmetric filter, care should be taken so that its orientation is correct. That is, the side with larger pore sizes of the asymmetric filter should encounter the unfiltered sample first. This orientation is important so that the liquid should pass through the filter and exit the side containing small pores and trapping the biological particulates in the matrix of the asymmetric filter. These filter membranes can have pore sizes of varying diameter depending on the application. In some embodiments, other orientations are possible. Different filter membranes of different materials and styles can be used as well. These materials can comprise, but are not limited to polycarbonate, polysulfone, polyester, polyethylene, and polypropylene.

Compound filters can also be used. A compound filter can include a second filter with a perimeter slightly smaller than the previously described filter, but still larger than the perimeter of the cutout in the double sided adhesive. The smaller filter is placed between the larger filter and the double sided adhesive. In this way, the adhesive binds to the perimeter of each filter membrane and seals each to ensure that fluid flows through the center of each filter instead of around the perimeter. This compound filter stack up design procedure can be performed indefinitely with more filters until the stack up becomes excessively thick or until the adhesive membrane can no longer seal to all of its intended surfaces. Another method to create a compound filter would be to use an additional array of both filter membrane and double sided adhesive in series to stack the filters in series. This additional array would be positioned between the output of the first filter membrane and the rigid support component. This allows for the creation of a filter with an indefinite number of filters in series. This process of stacking filters in series could potentially be done in combination with the previously mentioned method of using a slightly smaller filter to reduce the amount of double sided adhesive used.

The support component comprises a thin walled piece that mates with the adhesive and the filter membrane. Its perimeter is shaped so that it fits inside of the ridge located on the cap housing to achieve proper alignment. The support component comprises mini-channels that extend throughout the area of the filter material. The number and size of mini-channels can be minimized to reduce the amount of dead volume of filtered product. The mini-channels provide a low resistance path for the filtrate to travel to the exit hole that is connected to a mini-channel. Enough mini-channels can be incorporated so that the entire area of the exposed membrane can have access to a low resistance path to the exit hole(s). While multiple mini-channels are most commonly used, a single, serpentine channel can cover the same area as the multiple channels. In some embodiments, a spacing between channels is about 1.5 mm. Other spacing is also possible (e.g., 1-2 mm, 1-3 mm, 1-4 mm, 1 mm, 2 mm, 3 mm, etc.) The configuration of the channels can be selected based on the filter material and the roughness of the surface of the support component, as different filter materials will provide different levels of resistance for the product to travel to the nearest channel. A filter with smaller pores may have a smaller spacing between channels as compared to a filter with larger pores that provides a lower resistance path for the filtered product to travel to the channels.

Figure 3:
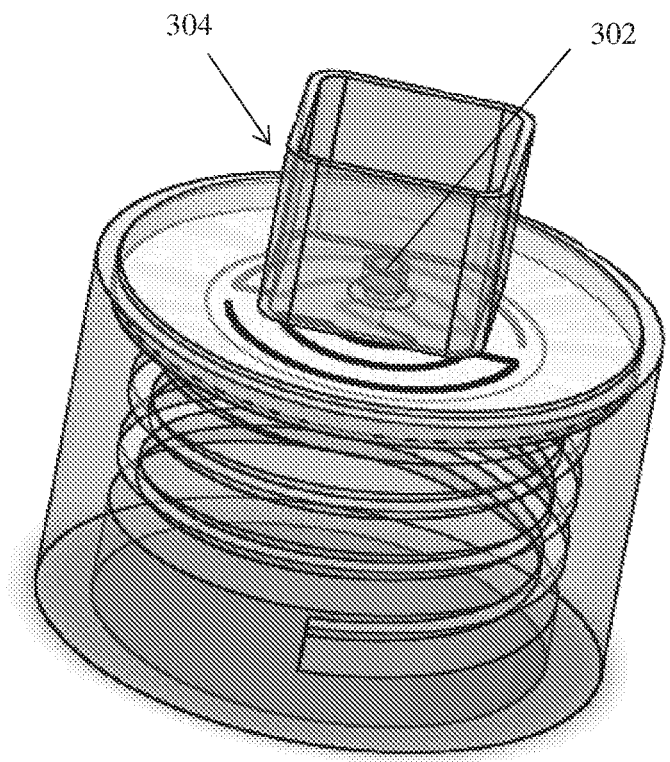
FIG. 3 depicts an embodiment of a cap of a sample filtration device.

The exit hole(s) can reside in any location connected to a mini-channel. The exit hole(s) can also comprise a spout feature. The spout feature is designed to control the fluid deposition and collection. This spout allows for precise dispensing of the fluid into a variety of receiving devices. The shape of a spout feature can be a barb, a capillary, a tapered nozzle, or a simple tubular feature. The wall thickness of the support component should take into account its resistance to bending so that when the device is pressurized, it does not provide significant bending. This can be achieved through material selection or designing a component with appropriate thickness. The materials for this component can be, but are not limited to, thermoplastics, metals, and ceramics. The support component can also comprise a protective sheath that helps control the interface with the collection device. This is especially valuable when depositing a sample into a point of care device. A transparent sheath 304, shown in FIG. 3, can be incorporated around the outlet 302 to prevent users from misaligning with the sample input area and ensure that full drops are formed instead of sometimes undesirably poured into the sample input area without forming full drops.

The flexible container is configured to house fluids before they are passed through the filter assembly. It also provides a pressure when the operator squeezes it which will then drive fluid through the filter assembly. The pressure required to drive the fluid through the device can be as low as 0.25 psi and can reach pressures up to 5 psi. If cell lysis is not desired, excessive pressure exceeding 5 psi are not be used for a blood sample, in some embodiments. An excessive driving pressure can cause cells to rupture and release intracellular content which may affect the result of the assay. The design of the flexible container is very similar to a generic squeeze bottle that contains threads at the top to mate with a cap. The materials to make the squeeze bottle can include, but are not limited to, high-density polyethylene, low-density polyethylene, polypropylene, and polyester.

To operate the device, unfiltered fluid is inserted into the flexible container. The container could have a removable seal at its opening to contain a prefilled amount of fluid inside while stored. If prefilled fluids are not desired for the application, then the operator can add the unfiltered fluid. If mixing is needed, then the operator needs to mix by inducing relative motion in the fluid. This can be done by stirring, swirling, or shaking the fluid. If any contaminated tools such as stir rods, swabs, or collection devices are used, they can be disposed of in the flexible container to prevent scattered waste. Once the sample is prepared, the operator ensures that the cap is sealed, inverts the assembly and points the spout feature into the desired location. The operator squeezes the flexible container to provide pressure and the filtrate exits the assembly until the desired quantity of filtrate is collected. The squeeze action drives fluid through the hole(s) in the cap housing and laterally to the entire exposed area of the filter membrane. The driving pressure forms a pocket between the filter membrane and the cap housing by pressing the membrane down against the rigid support component to prevent excessive stretching and tearing of the filter membrane. If an asymmetric filter is used, then the fluid enters into the membrane through the large pores and the filtrate exits through the small pores. Otherwise, the fluid passes through the pores of a symmetric filter membrane. All trapped particles remain trapped by the filter membrane. If a compound filter is used, then the filtered sample will filter again through the next filter membrane. The filtrate then travels from the exit of the membrane to the mini-channel(s). The filtrate flows along the mini-channel(s) to the exit hole(s) located on the support component. Finally, the filtrate exits in the assembly through the spout feature and is collected according to the desired application.

Figure 4:
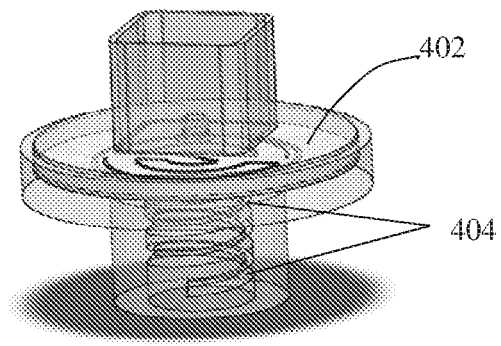
FIG. 4 illustrates another embodiment of a cap of a sample filtration device.

As shown in FIG. 4, in some embodiments, the size of the filter will need to be significantly larger than the opening of the flexible container. In order to accommodate a large filter 402 with a small flexible container the complimentary threads 404 are resized to be significantly smaller than the size of the entire perimeter of the cap housing. By doing so, a designer could make a filter of any size and shape to fit with any flexible container of any size and shape as long as complimentary threads on the cap housing and the flexible container match.

In some embodiments, there may be a desire to forego the use of the flexible container. In theory, this assembly could be used with any pressure generating device. Other pressure generating devices include a syringe, a pump, gravity fed tubing, or a pressurized accumulator similar to a gas cylinder. Therefore, the attachment does not need to include threads. For instance, the assembly could be designed with an input barb to mate with a tube. A double barbed assembly would produce an in-line filter that could be used in a different type of application. In another application, the assembly could incorporate a Luer tapered connection to attach to a syringe that is loaded with the sample to filter. In another application, the filter could contain a flat surface to connect to a pressure sensitive adhesive. This design is not limited to the use with the flexible container; however the use of a flexible container demonstrates the capabilities of the filter as an easy-to-use device. Furthermore, the use of a flexible container allows for the precise control of the driving pressure to reduce the risk of cell lysis as a result of excessive pressurization, which could more easily occur with a syringe.

In some embodiments, a buffer solution is mixed with the unfiltered fluid prior to filtration. Phosphate buffered saline (PBS) can be used as a buffer solution. Water can also be used; however, when using water, the osmotic pressure will drive excessive fluid into the cells and cause the cell membranes to rupture and release intracellular contents. This would include the hemoglobin and other intracellular components trapped in the cells, which would irreversibly dye the mixture a red color and release excessive protein into the sample mixture. Sometimes, lysis is desired if, for instance, DNA extraction from cells is required or to detect an intracellular biomarker. If lysis does occur, the filter can eliminate cell debris from the filtrate that may cause flowing problems in the assay. In traditional lateral flow immunoassay tests, the buffer may contain surfactants mixed into PBS to improve flow down the strip. Common surfactants used are Tween-20 and Triton-X100, however, Triton X-100 might cause cell lysis. In some embodiments, these surfactants are found on the strips themselves so that the buffer does not need to include it. Additionally, in some embodiments, the buffer solution may contain animal protein to prevent the analyte of interest from binding to the background by competing in those areas. The buffer solution can also contain an anticoagulant like EDTA to prevent blood clots from forming in the mixture.

The samples produced by the devices described herein can be used with any number of testing and diagnostic apparatuses, as the same principles could be used in all blood producing animal species including humans. As described above, protein detection using a lateral flow immunoassay (LFIA) test is contemplated. In some embodiments, the devices can be used for testing that is not protein based. For instance, this device could be used to perform a blood alcohol content test, cannabinoid detection in blood for *cannabis* consumption, measure a vitamin deficiency, or use it to isolate cell free DNA that circulates in the blood stream. Essentially, any analyte that circulates the bloodstream that is intercellular or intracellular can be tested by processing the blood with this device.

Filtering a whole blood samples using the devices and methods described herein can allow for reliable at home or in the field testing using lateral flow immunoassay test strips. Currently, people are using whole blood directly on test strips to fill this need. The problem with applying whole blood directly on test strips is that the red color of the blood sample introduces background noise that interferes with detection of the colloidal gold or fluorescent test line used in many lateral flow immunoassay diagnostic tests. Filtering out the cells from the plasma keeps the test strip free of background noise and allows easy detection of the test line. Reliable at home blood testing can be helpful for testing for diseases such as HIV, which may still carry a stigma in certain locations.

Figure 5:
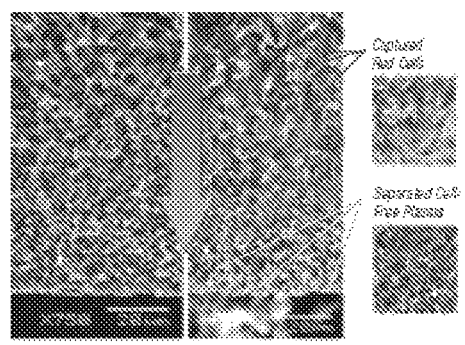
FIGS. 5 and 6 show embodiments of filter membranes.
Figure 6:
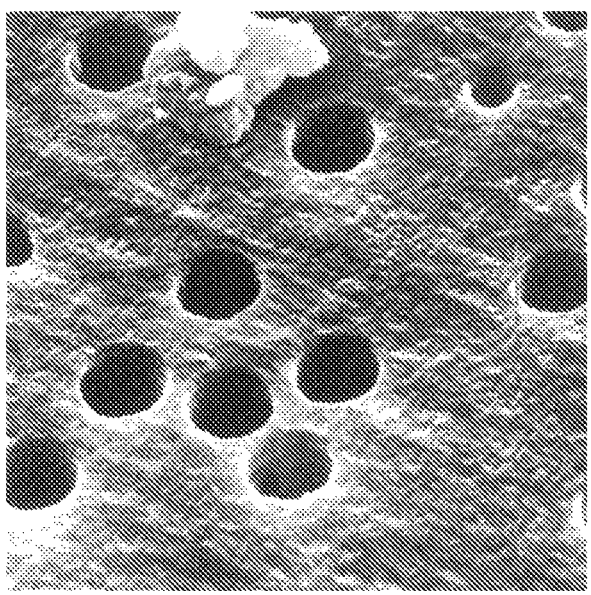

Different types of filters can be used depending on what is being measured. For example, to measure an analyte that circulates the bloodstream in the plasma, a single asymmetric filter can be used. In other embodiments, a compound filter can be used to selectively lyse specific populations of cells. In other embodiments, a rapid test for identifying sepsis-causing bacteria can work by detecting intracellular contents of the bacteria. In such embodiments, a 2 stage compound filter can be used. The first filter can be an asymmetric membrane filter (Pall MMM series, or Vivid series, or BTS series, shown in FIG. 5) designed to trap all of the large red and white blood cells without lysis. Because bacteria are usually smaller than blood cells, they would pass through this filter since the pores would be larger than the bacteria. Then, proceeding after the first filter membrane, a membrane filter with very small pores can be used. Such a filter can be designed to not only stop the bacterial cells but also lyse them. The second filter is not asymmetric like the first filter so as to allow fluid to flow around them. Instead, it can be configured as a membrane with holes penetrating through it (Whatman Nuclepore track-etched membrane, shown in FIG. 6) and the driving pressure would rupture the cells. This type of filter design would selectively lyse a population of cells while keeping other populations intact based on size. Another application for such a filter is to detect other blood borne parasites like malaria. With this method the assembly could potentially detect the intracellular contents of small immature malaria cells by selectively lysing them.

The research for finding biomarkers to detect for different conditions is rapidly changing and quickly improving. This device has the capability of processing a sample for both qualitative tests and quantitative tests, if known volumes of blood and buffer are inserted into the device.

Qualitative tests provide a binary positive/negative result. Examples of qualitative tests that can be used with the devices herein include: detecting hCG hormone for pregnancy; detecting HIV antibody and/or surface antigen for HIV infection; detecting Hepatitis antibody and/or surface antigen for Hepatitis A/B/C infection or vaccination; detecting Herpes antibody for Herpes infection; detecting EIAV antibody for Equine infectious anemia in horses; detecting Heartworm antigen in dogs/cats for detecting heartworm disease; and detecting the presence of legal/illegal drugs in the bloodstream. In some embodiments, such as in a test detecting HIV antibody, the filtration device described herein can enable simple at home or in the field blood testing of HIV antibody earlier than current saliva based tests. In some embodiments, the filtration device described herein can enable simple at home or in the field blood testing of hCG earlier than currently available home urine based tests.

Quantitative tests provide a numerical value for the concentration of an analyte in the blood. This type of test is substantially more difficult to perform because it is critical to ensure that the volumes are properly collected and processed. A few examples of quantitative tests that can be used with the devices and methods described herein include measuring a sudden spike in Luteinizing Hormone for ovulation tracking; measuring an high concentration of H. Pylori antibody for ulcer diagnosis; measuring PSA concentration for prostate cancer screening; measuring Parathyroid hormone concentration for detecting a parathyroid adenoma; measuring HDL/LDL concentrations for monitoring cholesterol; and measuring Creatinine concentration for monitoring kidney function.

In some embodiment, quantitative tests employing a comparison of a test line to a control line can be enhanced using a smartphone application configured to compare the intensity of the lines. In some embodiments, a quantitative test uses a swab configured to hold about 20-30 µL. A buffer solution used can provide a 1:10 dilution to ensure sufficient volume for the quantitative test.

Figure 7A:
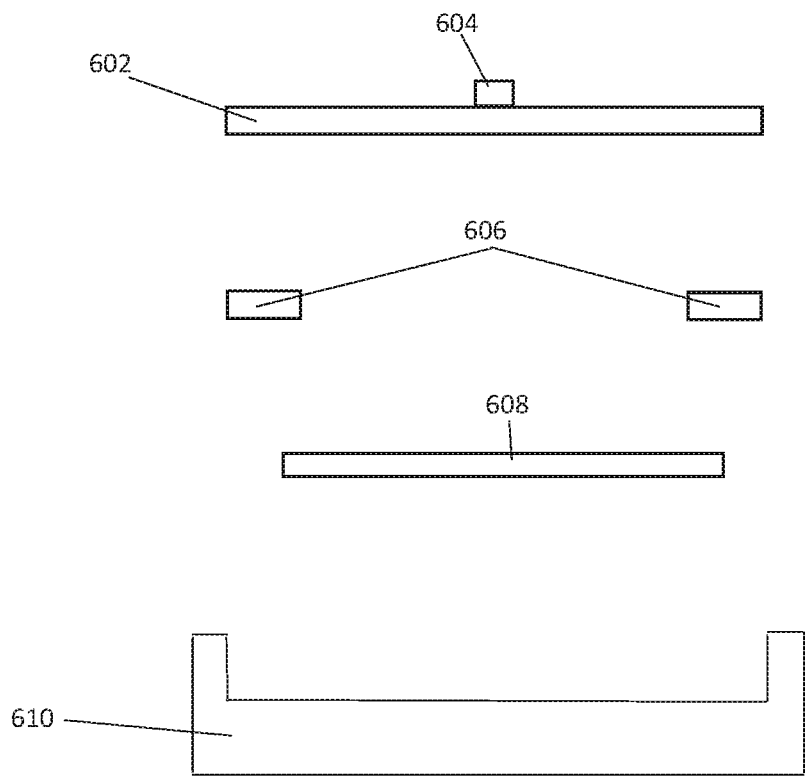
FIGS. 7A and 7B depict an embodiment of a manufacturing process for a sample filtration device.
Figure 7B:
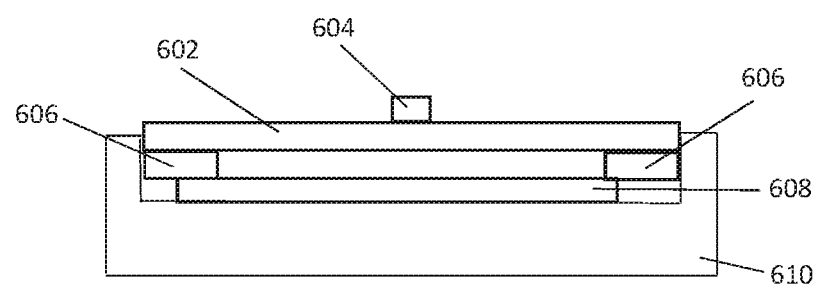

FIGS. 7A and 7B illustrate an example manufacturing process for components of the devices described herein. FIG. 7A shows an exploded side view of an output substrate 602 including outlet 604 or spout, a double sided adhesive 606, a filter 608 and an input substrate 610. A manufacturing process includes adhering a top side of the adhesive 606 to a bottom side of the output substrate 602. A bottom side of the adhesive 606 is adhered to a top side of the filter 608 and a top surface of the inner portion of the input substrate 610. Traditionally, most filters use ultrasonic welding so the manufacturing process time depends on plastic melting time, etc. In this case, the filter is manufactured using adhesive, so the manufacturing process can be much faster.

While above figures depict the filter assembly being assembled on a lid of a flexible container, the following figures depict a filter assembly being assembled together with a flexible connector. The following embodiments of sample filtration devices (e.g., those described with respect to FIGS. 8A-17) can comprise the features of the filter described with respect to FIGS. 1A-7B. The flexible connector can be used to connect the filter to various sample collection and dispensing devices (including squeeze bottles). The flexible connector can allow for the use of the sample filtration device in many different types of applications including whole blood filtration. The flexibility in the material of the flexible connector can allow it to conform to different types of attachment features thus making it adaptable to many applications. As noted, the flexible connector described permits the use of conventional sample collection and dispensing devices to interface with it. These devices include, but are not limited to, bulb pipettes, micropipette tips, capillaries, syringe needles, barbs, squeeze bottles, tubes, and other devices with tubular or tapered interfacing geometries. In addition, it also can interface with noncircular geometries and components that contain manufacturing artifacts like parting lines and flash (e.g., bulb pipette, described below).

Figure 8A:
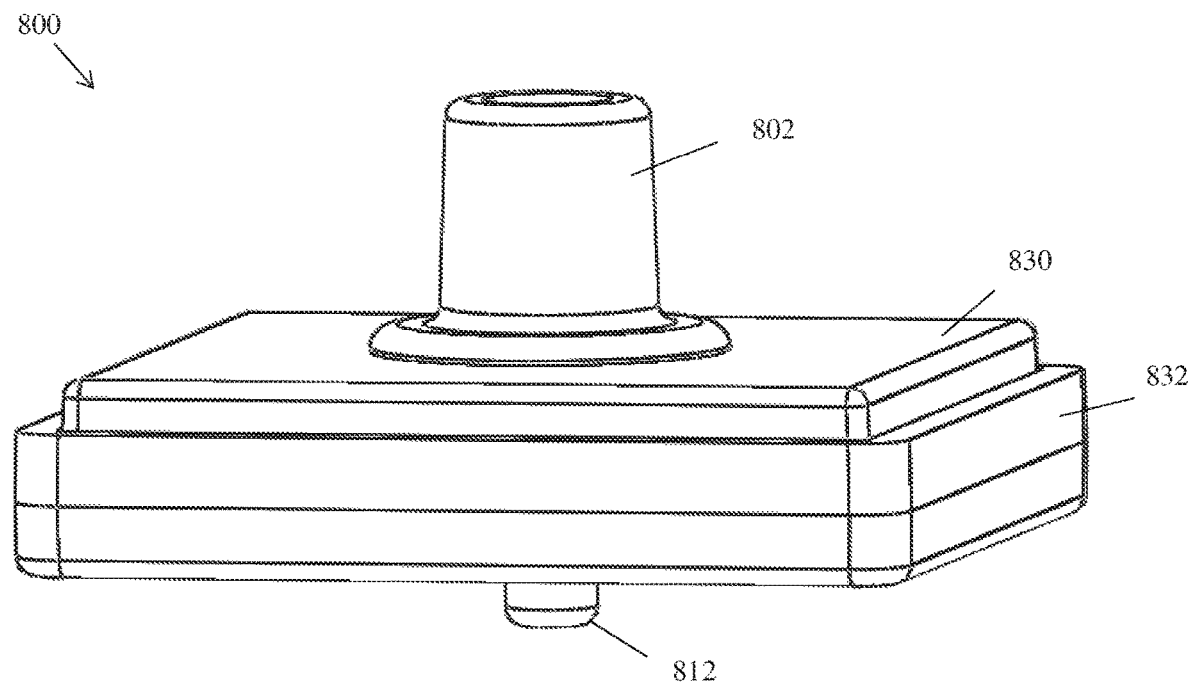
FIGS. 8A-8E illustrate an embodiment of another sample filtration device.
Figure 8B:
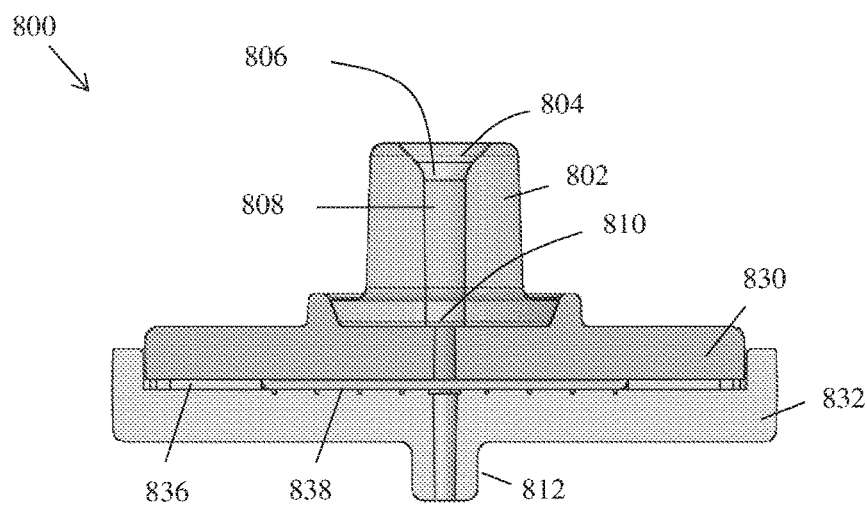
Figure 8C:
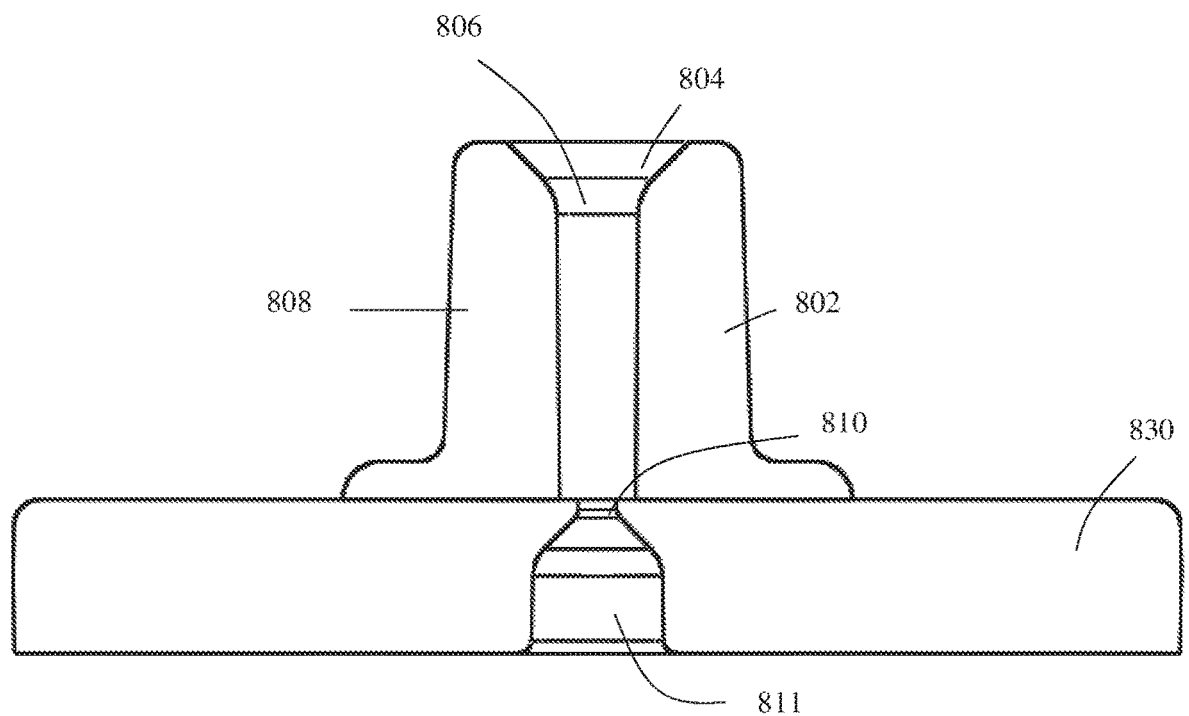

FIGS. 8A-8C illustrate various views of an embodiment of a filter assembly 800 comprising a flexible connector 800 that can be used with the filter (e.g., the filters described herein). FIG. 8A shows a perspective view of a filter assembly flexible connector 802 attached to an input substrate 830 of the filter assembly. Beneath the input substrate 830 is an output substrate 832. As shown in the front section view of FIG. 8B, the filter membrane 838 and adhesive layer (e.g., double sided adhesive layer) 836 are positioned between the input substrate 830 and the output substrate 832. In some embodiments, the adhesive layer 836 and filter membrane 838 are in reverse order. For example, the filter membrane 838 lies above or below the adhesive layer 836 while ensuring that the correct orientation of the filter membrane is preserved.

In some embodiments, the filter membrane comprises a length of about 17 mm and a width of about 17 mm. Other dimensions are also possible (e.g., width and/or length of about 15 mm, 16 mm, 17 mm, 15-20 mm, 10-15 mm, greater than 20 mm, etc.). In some embodiments, the adhesive layer comprises a double sided pressure sensitive adhesive layer. The adhesive layer can comprise a pressure sensitive adhesive layer disposed on either side of a substrate (e.g., a PET substrate). Each adhesive layer can comprise a thickness of about 0.005". Other dimensions are also possible (e.g., about 0.004-0.006", about 0.003-0.007", about 0.002-0.008", about 0.004", about 0.006", etc.). The substrate can comprise a thickness of about 0.005". Other dimensions are also possible (e.g., about 0.004-0.006", about 0.003-0.007", about 0.002-0.008", about 0.004", about 0.006", etc.). An adhesive layer with a 0.005" adhesive layer positioned on either side of a 0.005" substrate comprise a total thickness of about 0.015".

This thickness leaves a very thin 0.002" gap with a filter membrane comprising dimensions of 17 mm×17 mm, to permit fluid to flow laterally and wet the entire filter. It can be important to minimize this gap to ensure that enough pressure builds up in the assembly to drive the sample through the filter but still sufficient to permit fluid to flow laterally to reach the entire exposed filter membrane. Oversizing the gap can cause incomplete filtration of the sample due to insufficient drive pressure by introducing empty volume. If insufficient gap is present, then sample may encounter a restricted flow path to reach the entire exposed filter membrane. Proper design of this gap allows for the low volume of air dispensed by the pressurization device to ensure that the liquid sample is filtered completely. For instance, a 100-1000 µL micropipette typically can only dispense about 250 µL of air upon reaching the second stop of the plunger after dispensing the liquid volume. Minimizing this gap permits the use of low air volume dispensing devices, like a micropipette, to be used as a pressure source to properly drive the sample through the filter assembly completely. Other gap dimensions are also possible (e.g., about 1-3 mm, about 1 mm, about 3 mm, etc.).

The adhesive layer can comprise a length and width of about 22 mm. Other lengths and widths are also possible (e.g., about 21 mm, about 23 mm, about 21-23 mm, about 20-24 mm, about 19-25 mm, about 15-25 mm, greater than 25 mm, etc.). The cutout in the adhesive layer can comprise a length and width of about 14 mm. Other lengths and widths are also possible (e.g., about 13 mm, about 15 mm, about 13-15 mm, about 11-17 mm, about 10-20 mm, etc.)

In some embodiments, one or both of the input substrate and the output substrate comprises polycarbonate. Other materials are also possible (e.g., polypropylene, polyethylene, and polystyrene.) Polycarbonate can advantageously be chemically compatible with the flexible connector material when it is being overmolded with a thermoplastic elastomer (TPE) with a durometer Shore 50A. This compatibility can ensure that the flexible connector material stays properly secured on the substrate and does not introduce leak paths. The input substrate can comprise a thickness of about 3 mm. Other dimensions are also possible (e.g., about 2 mm, about 4 mm, about 2-4 mm, about 1-5 mm, etc.). The input substrate can comprise a width and length of about 22 mm. Other lengths and widths are also possible (e.g., about 21 mm, about 23 mm, about 21-23 mm, about 20-24 mm, about 19-25 mm, about 15-25 mm, greater than 25 mm, etc.). In some embodiments, a surface of the input substrate is flat to adhere to the double side adhesive. In some embodiments, the surface of the input substrate comprises proud or textured features. In some embodiments, the output substrate comprises a thickness of about 2 mm. This thickness can be sufficient to prevent bending during pressurization. Other thicknesses are also possible (e.g., about 1 mm, about 3 mm, about 1-3 mm, about 1-5 mm, etc.). The output substrate can comprise a length and width of about 22.25 mm. These dimensions can allow a 22 mm×22 mm input substrate to fit within an area of the output substrate with the adhesive layer and filter membrane positioned between the input and output substrates. Other lengths and widths are also possible (e.g., about 21 mm, about 23 mm, about 21-23 mm, about 20-24 mm, about 19-25 mm, about 15-25 mm, greater than 25 mm, etc.)

At the top of the flexible connector 802, a funnel 804 can be included to allow for easy attachment to the connector. The funnel 804 leads the attaching feature into the hole 806 (best shown in FIG. 8C). In some embodiments, the funnel comprises a large diameter of about 3.6 mm, a small diameter of about 1.6 mm, a chamfer angle of 45°, and a length of about 1 mm. Other dimensions are also possible. For example, the large diameter can be about about 3-4 mm, about 3 mm, about 4 mm, about 2-6 mm, etc. The small diameter can be about 1-2 mm, about 1 mm, about 2 mm, about 0-3 mm, etc. The chamfer angle can be about 40-50°, about 35-55°, about 30-60°, etc. The length of the funnel can be about 0.75-1.25 mm, about 0.5-1.5 mm, about 0.75 mm, about 1.25 mm, etc.) After the chamfer of the funnel 804, is a narrow tube or pipe 808. This pipe can be long enough that it is able to grip and seal onto the attaching feature (e.g., the end of a pipette tip). The pipe can be about 7 mm high. Other lengths are also possible (e.g., about 5-7 mm, about 5 mm, about 6 mm, about 6-8 mm, about 5-9 mm, about 7-8 mm, about 7-9 mm, etc.). The pipe can have a minimum inner diameter of about 1.5 mm. Other geometries are possible (e.g., about 1 mm, about 1-2 mm, about 2 mm, etc.). A pipe with a length of about 7 mm and a minimum inner diameter of about 1.5 mm can be configured to both grip and seal to a commercial 1000 μL pipette tip as well as many other inserted connecting features.

After the pipe 808, there is a contracting hole 810 that prevents further insertion into the assembly. This contracting hole 810 prevents damage to the filter membrane caused by over-insertion of the connecting male feature into the flexible connector. In some embodiments, the contracting hole comprises a diameter of about 0.75 mm. Other diameters are also possible (e.g., about 0.7 mm, about 0.8 mm, about 0.6-0.9 mm, about 0.5-1 mm, etc.). The contracting hole 808 is sized smaller than the tip of the connecting feature (e.g., pipette) so that it comes to an abrupt stop once it encounters the contracting hole 808, but before it reaches the filter membrane.

The flexible connector can comprise a flexible material including, but not limited to TPE, silicone, rubbers, polyurethane, and soft thermoplastics such as LDPE, HDPE, PP, and plasticized PVC. The wall thickness of the flexible connector is such that it provides enough rigid support when a connecting device attaches to the flexible connector so that it maintains alignment while still permitting for slight misalignments. It is also sized so that it can provide rigidity when inserting into a bore such as in the neck of a squeeze bottle. In some embodiments, the wall thickness is 2 mm. Other thicknesses are also possible (e.g., 1.5-2.5 mm, about 1.75-2.25 mm, about 1-3 mm, about 1-4 mm, etc.).

On the opposite end of the flexible connector is an output feature 812 that directs the fluid into a desired location. The feature is sized so that it protrudes only slightly (e.g., about 2 mm, about 1-3 mm, about 1 mm, about 3 mm, greater than 3 mm, etc.). This allows for easy alignment and attachment to a commercial test cartridge, which can be a challenge in other available filter designs. The flat surface on the output side mates to the surface of a flat test cartridge so that the fluid is always directed perpendicularly into the cartridge. The small protrusion length and diameter of the output feature can provide clearance when residing in the sample input feature of a test cartridge. The outer diameter of the output feature can be about 1.25 mm. Other diameters are also possible (e.g., about 1 mm, about 1.5 mm, about 1-1.5 mm, about 0.5-1.5 mm, about 0.5-2 mm, about 1-2 mm, about 1-3 mm, etc.). This feature can also ensure that fluid does not stick to the walls of the filter assembly and is directed primarily into the test cartridge.

Figure 8D:
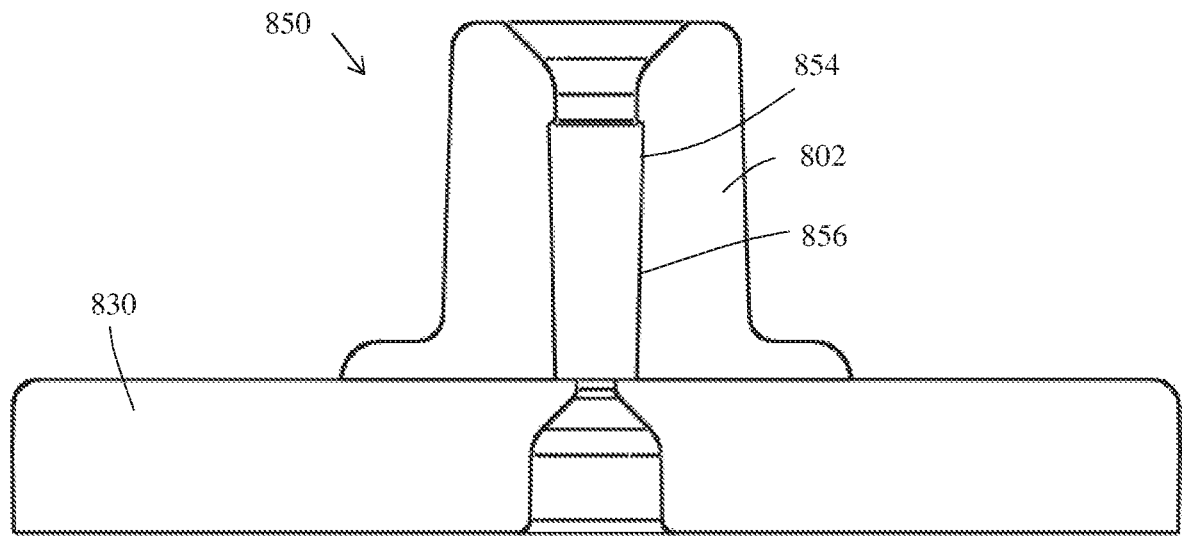

FIG. 8C illustrates an embodiment of a flexible connector 802 connected to an input substrate 830. The flexible connector comprises funnel portion 804, opening 806, pipe 808, and contracting hole 810. The embodiment of FIG. 8C differs from that shown in FIG. 8B as there is a larger cavity 811 beyond contracting hole that can be used to house a ball valve, as described in further detail below. FIG. 8D illustrates an embodiment of a filter assembly 850, similar to the assembly shown in FIG. 8C, but the flexible connector 852 of FIG. 8D includes an undercut 854 at the top of pipe 856. This undercut 854 can provide an audible snap when a barb is connected to the flexible connector. The undercut 854 can also hold the barb in place connected to the filter assembly.

Figure 8E:
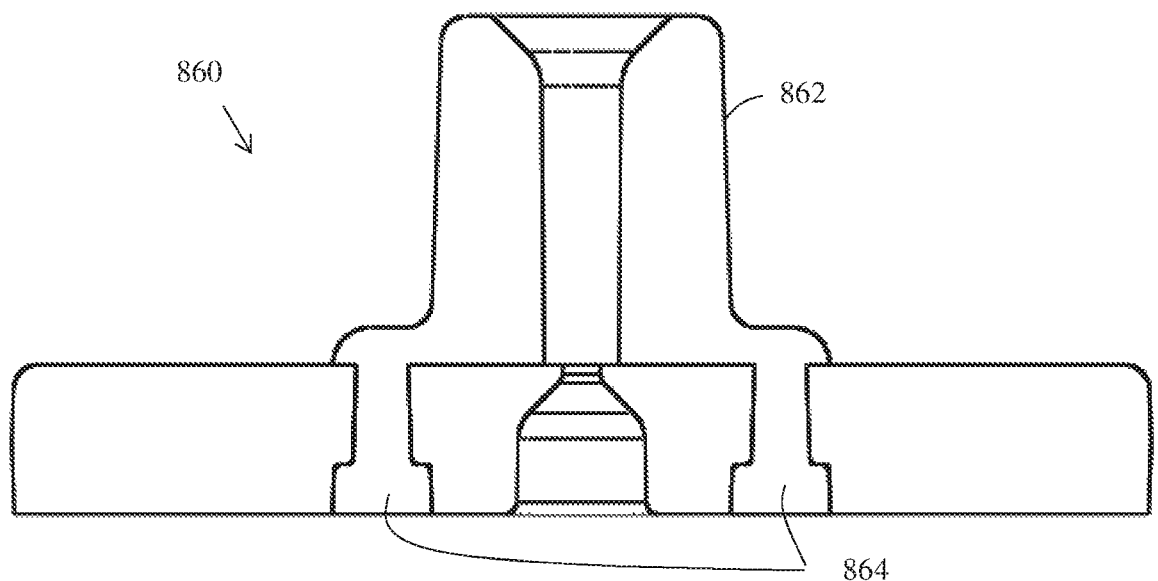

FIG. 8E illustrates another embodiment of a flexible connector 862 connected to an input substrate 864. The connector 862 and substrate 864 are connected using mechanical interlocks 864 which can help prevent the flexible connector from separating (e.g., peeling apart) from the input substrate.

In some embodiments, the filter assembly is formed as one piece or can be formed as separate pieces that are connected. In some embodiments, the polycarbonate substrate can be injection molded and then physically placed onto another mold. The flexible connector material (e.g., elastic TPE) can then be overmolded onto the substrate to create the flexible connector.

Figure 9A:
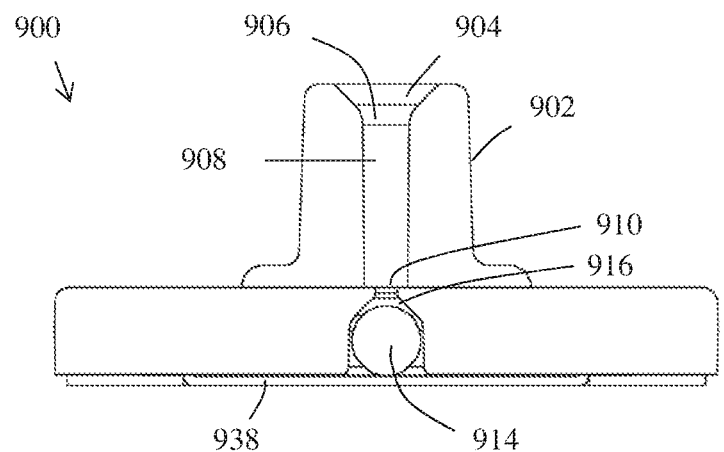
FIGS. 9A-9B show an embodiment of a sample filtration device.
Figure 9B:
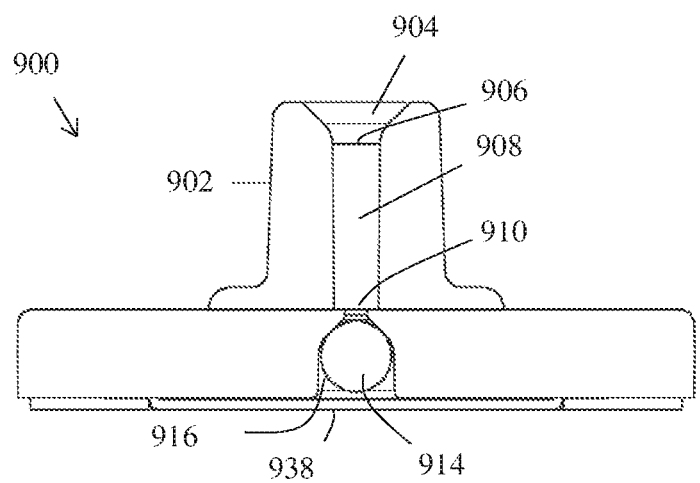

As shown in FIGS. 9A and 9B, in some embodiments, the filter assembly 900 comprises a ball valve. The valve feature can address the back flow caused when an operator releases the activation action such as releasing a squeeze bottle or releasing the plunger of a micropipette. As in the embodiment shown above, the filter assembly comprises flexible connector 902, funnel 904, opening 906, pipe 908, and contracting hole 910. The ball 914 rests in a cavity 916 that provides clearance and is disposed just past the contracting hole. One of the walls of the cavity is formed by the filter membrane 938 and the ball rests on the filter when it is not in use. Upon activation of the pressurization action, the ball does not plug the cavity; however, upon release of the activating action, fluid will flow backwards. This is because actions like the release of a squeeze bottle will create a negative relative pressure that will suck back the fluid as the squeeze bottle tries to return to the original shape. Therefore, including a ball in the design of the filter will prevent back flow because the ball will create a seal in the cavity, sealing contracting hole 910. FIG. 9A shows the valve in an unsealed configuration with a fluid path around the ball 914 from the pipe 908 to the filter membrane 938, while FIG. 9B shows the valve in a sealed configuration with the ball 914 sealing the fluid path between the filter membrane 938 and the pipe 908. The ball can comprise different materials that include, but are not limited to rubbers, plastics, ceramics, and metals. In addition, a user can select a material with a density such that the ball will either float or sink depending on the orientation that the assembly is held. For example, a polypropylene (density ~0.9 g/cm$^3$) material floats in water making it easier to seal in an upright orientation. However, a nitrile (density ~1.3 g/cm$^3$) rubber ball will sink if the filter is held upside down making it a better sealing material in that orientation. The negative relative pressure generated by the pressurization device will then maintain the seal by creating a pressure differential on opposite sides of the ball, which seals the input, hole and prevents backflow.

Figures 10A, 10B:
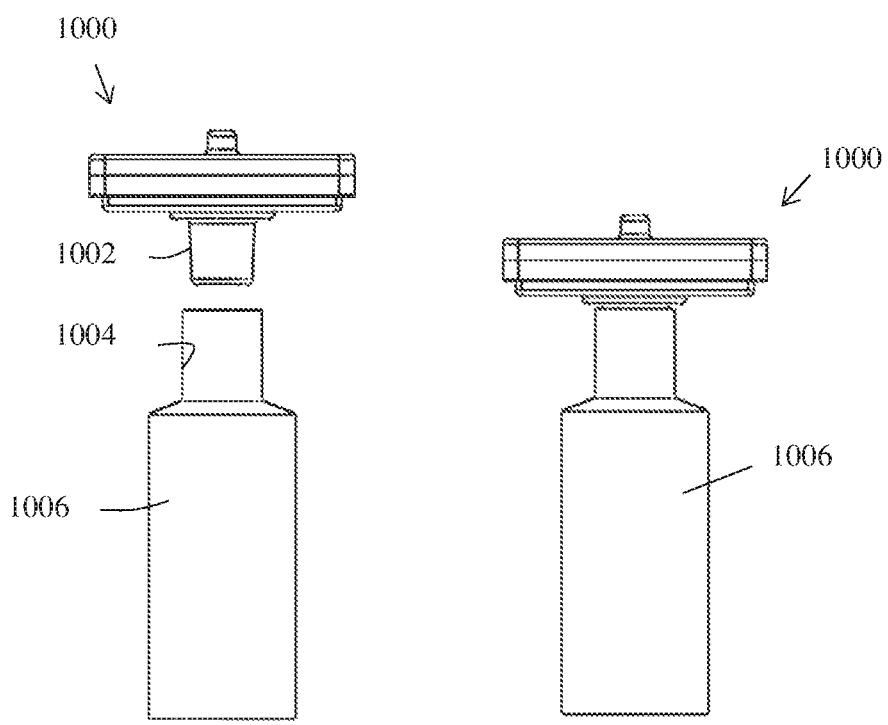
FIGS. 10A-10B depicts an embodiment of a sample filtration device connecting to a flexible container.

FIGS. 10A-10B show how the flexible connector can be used to attach the filter assembly 1000 to a squeeze bottle 1006. The flexible connector 1002 can be inserted into and seal against the inside 1004 of the inner diameter of the bottle. The inner diameter of the bottle 1004 provides an interference with the connector once inserted and allows the device to be operated in as described above (e.g., in FIGS. 1A-1B).

The funnel feature of the flexible connector can be especially useful when attaching a micropipette tip to the flexible connector. A micropipette is held far away from the end of the pipette tip, so aiming the tip into the flexible connector is significantly more difficult without using a funneling feature as shown in the image. As noted above, a filter assembly with a pipe that is about 7 mm high and has a minimum inner diameter of 1.5 mm can allow the flexible connector to both grip and seal to a commercial 1000 µL pipette tips as well as many other inserted connecting features.

Figure 11A:
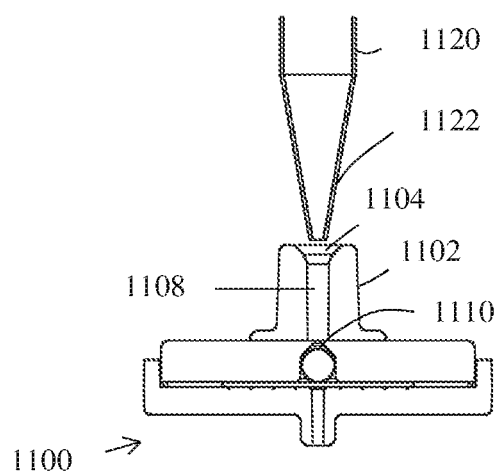
FIGS. 11A-11B illustrate an embodiment of a micropipette inserted into a sample filtration device.
Figure 11B:
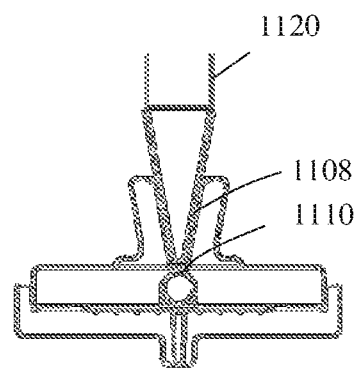

FIGS. 11A-11B illustrate an example of a micropipette being used with the filter assembly 1100. A 100-1000 µL micropipette 1120 collects a sample (e.g., 100 µL) of whole blood. The tip 1122 is then inserted into the funnel 1104 of the flexible connector 1102. Upon insertion, the flexible connector creates a fluidic seal on the tip, as shown in FIG. 11B. The connection between the connector and the micropipette also permits the entire assembly to be lifted and transported to the appropriate location for use.

FIGS. 12A-12C show a micropipette inserted into a filter assembly 1200, with the plunger of the micropipette depressed to various positions. FIG. 12A shows the micropipette 1210 inserted into the flexible connector 1202 prior to pressing of the plunger 1214. The plunger of a common lab micropipette has 2 stops. Depressing the plunger to the first stop, as shown in FIG. 12B, dispenses the contents of the pipette tip. Depressing the plunger to the second stop, as shown in FIG. 12C, ejects any remaining liquid by expelling air. In FIG. 12C, the micropipette is depressed up to the second stop using the expelled air as a source of pressure to apply on the blood to drive it through the filter. Once an appropriate amount of plasma has been dispensed, the user can release the plunger to release the pressure on the assembly. In some embodiments, the plunger is held for 1 minute, but could be held for longer or shorter depending on the application. In other applications, the same mode of operation can be used to filter diluted blood as well. Generally, diluted blood can be filtered faster since there are fewer cells to clog the filter. In some embodiments, diluted blood can be filtered by holding the plunger for about 5 s. In other embodiments, the plunger can be depressed for a shorter or longer amount of time when filtering diluted blood. As described in connection with FIGS. 12A-12C, a common lab micropipette 1210 can be easily adapted to filter diluted blood in addition to whole blood without the need of centrifugation using the filter assembly of the current application. The expelled air and liquid volume of a micropipette is a precise amount and can be used to provide a reliable pressure on the blood to filter the contents.

Additionally, as shown in FIGS. 12D-12G, a bulb pipette 1240 can be inserted into the flexible connector 1242. The design of the flexible connector can address the challenge posed by the parting line and flash of the bulb pipette introducing a leak path when sealing to other materials. By using a bulb pipette with the flexible connector, the parting line no longer poses a problem for sample leakage. This is because the flexible property of the flexible connector allows it to seal on non-ideal surfaces. Molding flaws such as parting lines and flash introduce non-ideal sealing surfaces that pose problems with sealing against rigid or semi-rigid materials by introducing microscopic leak paths. The flexible material of the flexible connector is able to conform to the irregular and non-ideal surfaces and molding flaws to seal them and reduce the potential of undesired leaking.

As shown in the following figures, the filter assembly can be placed directly on a cartridge containing latch, or adhesive, or bonding features so that the assembly is secured in place while the cartridge is packaged by the test cartridge manufacturer. The user would be able to apply their preferred sample processing device (micropipette tip, bulb pipette, squeeze bottle with an appropriate male connector, etc.) directly on the cartridge. This mode of operation would remove the need for alignment because the fluid is delivered directly on to the after the processing device is secured in place. Furthermore, the flat nature of the design of the assembly allows for easy assembly and packaging. Typically, commercial filter assemblies contain long protruding features, which make them difficult to adapt into a cartridge. In the current design, the surfaces of the device are flat and protruding features are minimized in their impact to allow for simple integration to a variety of applications. FIGS. 13A-13B show perspective views of an embodiment of a filter assembly 1300 attaching to a cartridge 1302. FIG. 13A shows the filter assembly 1300 and cartridge 1302 prior to placing the assembly 1300 on the cartridge 1302. The cartridge 1302 comprises latch features 1304. The filter assembly can be properly positioned on the cartridge using aligners 1305 and latch features 1306 and snapped onto the cartridge with the protrusions 1306 of latch features 1304 securing the filter assembly in place. The aligners 1306 and latch features properly align the output of the filter assembly with the sample input area 1308 of the cartridge 1302 as shown in FIG. 13B. FIGS. 13C and 13D are side section views of filter assembly 1300 and cartridge 1302. The output feature 1312 of the filter assembly is seen in the side views of FIGS. 13C and 13D. FIG. 13C shows the filter assembly 1300 and cartridge 1302 prior to placement of the filter assembly 1300 on the cartridge 1302. FIG. 13D shows the filter assembly 1300 placed on the cartridge 1310 using aligners 1305 (not shown in FIG. 13D) and latches 1304. FIGS. 13A-13D show the latches snapping onto the output substrate of the filter assemblies, but the latches can snap to the input substrate of the filter assembly in some embodiments. Other attachment mechanisms are also possible (e.g., Pressure sensitive adhesive, liquid adhesives, ultrasonic welding, crush ribs, crush pins, and press fits).

Figure 13E:
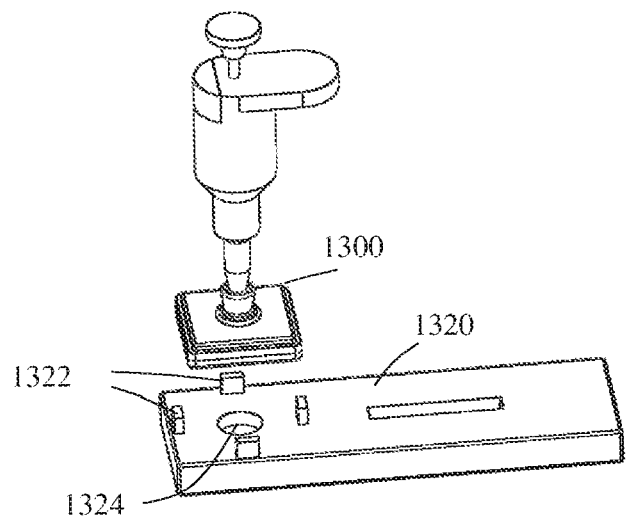
Figure 13F:
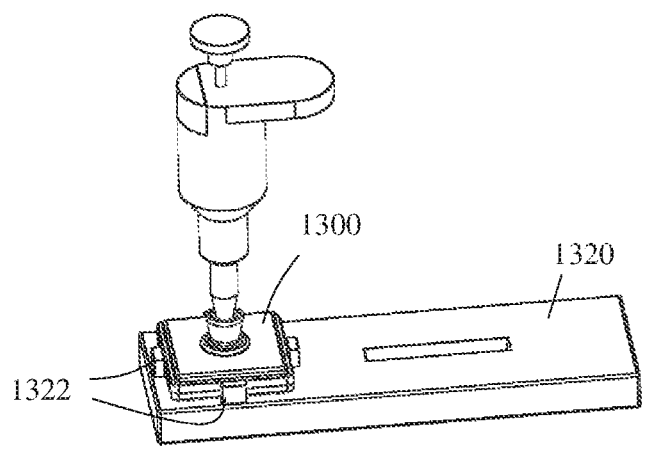

FIGS. 13E and 13F show perspective views of a filter assembly 1300 being used with another embodiment of a cartridge 1320. FIG. 13E shows the filter assembly 1300 prior to placement on the cartridge 1320. In this embodiment, the cartridge 1320 comprises aligners 1322, but the aligners do not comprise protrusions to form latches. The aligners can be used to properly position the filter assembly over the sample input area of the cartridge, as shown in FIG. 13F. The filter assembly can be aligned to the cartridge, the filtrate dispensed, and the filter assembly removed from the cartridge, so that the filter assembly and micropipette tip are disposed of separately from the cartridge. In some embodiments, as shown in FIGS. 13E and 13F, the filter assembly need nor remain attached to the test cartridge. This mode of operation permits users the flexibility of keeping the filter assembly attached or detached from the cartridge as the application requires. For example, if the cartridge is later inserted into an analyzer, the filter assembly may physically interfere with the cartridge insertion. Additionally, disposing of the filter assembly separately reduces the probability of contaminating the analyzer. In some embodiments, the aligners can be used in combination with a pressure sensitive adhesive or bonding agent to attach the filter assembly 1300 to the cartridge 1320.

Figure 14A:
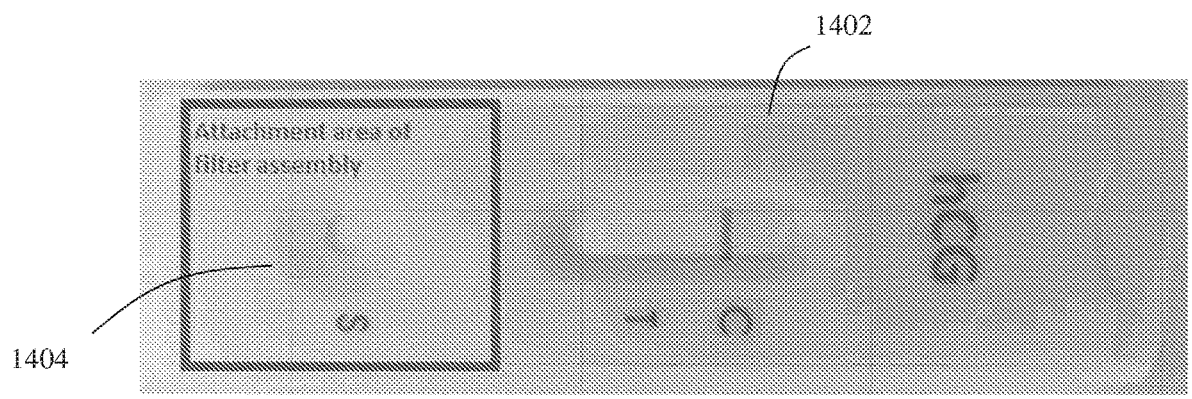
FIGS. 14A-14B illustrate embodiments of test cartridges that can be used with sample filtration device disclosed herein.
Figure 14B:
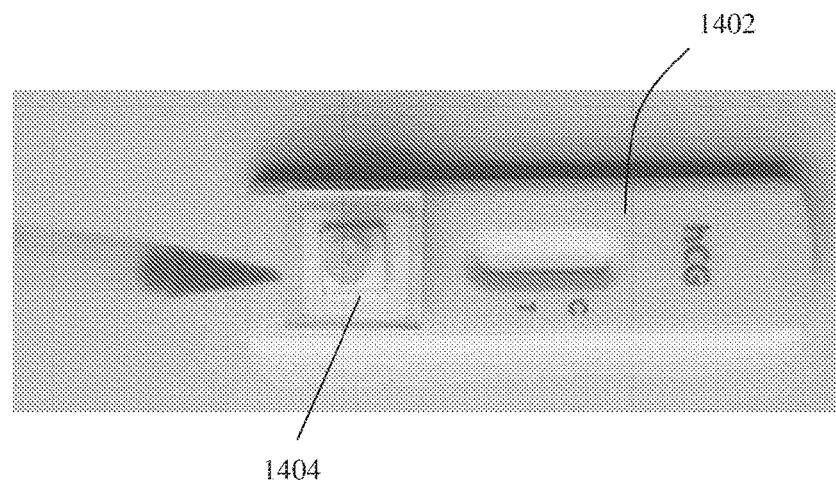

FIG. 14A illustrates an embodiment of a commercial test cartridge 1402 and the location at which the filter assembly would be attached (e.g., the sample input area 1404). FIG. 14B shows the filter assembly 1400 attached to the cartridge 1402.

Figure 15:
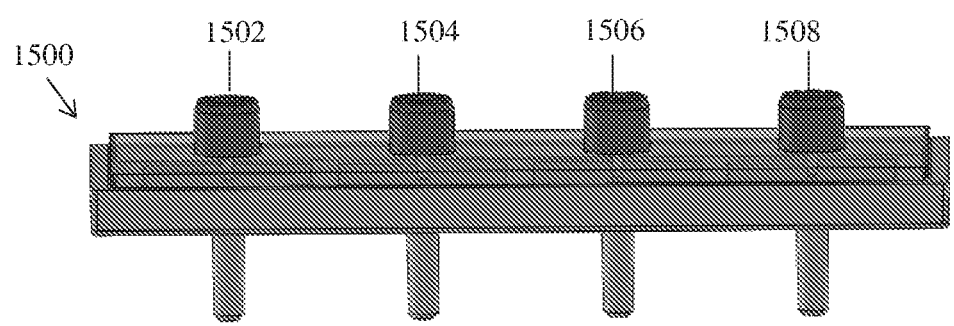
FIG. 15 shows an embodiment of an array comprising sample filtration devices disclosed herein.

As shown in FIG. 15, in some embodiments, the filter design can be assembled in an array for a multichannel micropipette or a robotic liquid handling station. This configuration can be especially useful to save time in the lab when multiple samples need to be processed at once. FIG. 15 shows how the filter assembly can be adapted into an array where all four ports 1502, 1504, 1506, 1508 act independently from each other allowing different samples to be filtered independently without cross-contamination. Each port 1502, 1504, 1506, 1508 can comprise the flexible connector and filter assembly design described above. This design can be expanded to any number of filters in an array. The standard and ubiquitous 96 well plate format common across lab equipment has 9 mm spacing between each of the pipette channels. The input channels can be spaced 9 mm apart or any multiple of 9 (9, 18, 27, etc.).

FIGS. 16A-C depict other embodiments of a filter device utilizing a flexible container 1602 and cap 1604 design as described above (e.g., with respect to FIGS. 1A and 1B). To improve the usability of the blood filter design with flexible container, a swab 1606 can be included in the cap 1604 as shown in the cross section of FIG. 16A. The swab length is sized so that when the user begins to twist the cap 1604, the tip 1608 of the swab is pressed up against the inner wall of the squeeze bottle 1602. The swab 1606 is ideally made of a semi-rigid and bendable material and geometry so that it does not break when the forces are applied during the attachment of the cap 1604. The twist action of turning the threads 1610 of the cap on the threads 1612 of the bottle ensures that the cap is locked in place while also agitating the fluid so that the blood sample that is on the swab tip is mixed with the buffer solution inside of the bottle.

It was found that when turning threads clockwise to attach the cap with the swab, the cap would recoil in the counter-clockwise direction due to the elasticity in the swab when bent. To counteract this recoil, friction between the threads of the cap 1610 and the threads of the flexible container 1612 was introduced so that the recoil torque applied to the cap 1604 does not turn the cap 1604 significantly in the opposite direction. The swab 1606 is secured onto the cap 1604 by including an undercut 1614 in the swab, shown best in the magnified view of FIG. 16B. Can you please confirm this is correctly referenced in the figure? This undercut 1614 snaps into place with complimentary mating features 1616 on the cap 1604. It is important that the cap is able to transmit a torque to the swab so that it rotates while turning. Therefore, the undercut comprises facets 1618 to permit the transmission of torque. The cap also includes complimentary facets 1620 to mate with the cap.

Another important feature for this to function properly can be that the cap and swab must not create a fluidic seal when attached to permit the sample into the filter. Therefore, there can be a mismatch in geometry between the swab 1606 and the cap 1604. In this example, the hex flat to flat dimensions (e.g., a distance between parallel facets of the hex) of the cap 1622 exceed the hex outer flat to flat dimensions 1624 (by e.g., 0.002", 0.001-0.002" 0.001-0.1", 0.001-0.005", etc.) to permit fluid to flow through the gap and into the filter. The swab is snapped into place by pushing the latch features 1614 on the swab beyond the hex 1620 in the cap. These latch features ensure that the swab is held in place and cannot be easily pulled out. If the filter is placed on the test cartridge itself or if the application does not require filtration, then there will be no need for the filter on the cap and fluid will flow freely out once the device is squeezed. The above configuration demonstrates how to integrate the filter into this assembly, but a filter is not required when a test does not require sample filtration. Instead, this description depicts a method of mixing a sample of blood using a screw cap with the option to integrate with a filter design so that it can be dispensed as a filtered or unfiltered sample.

Figure 17:
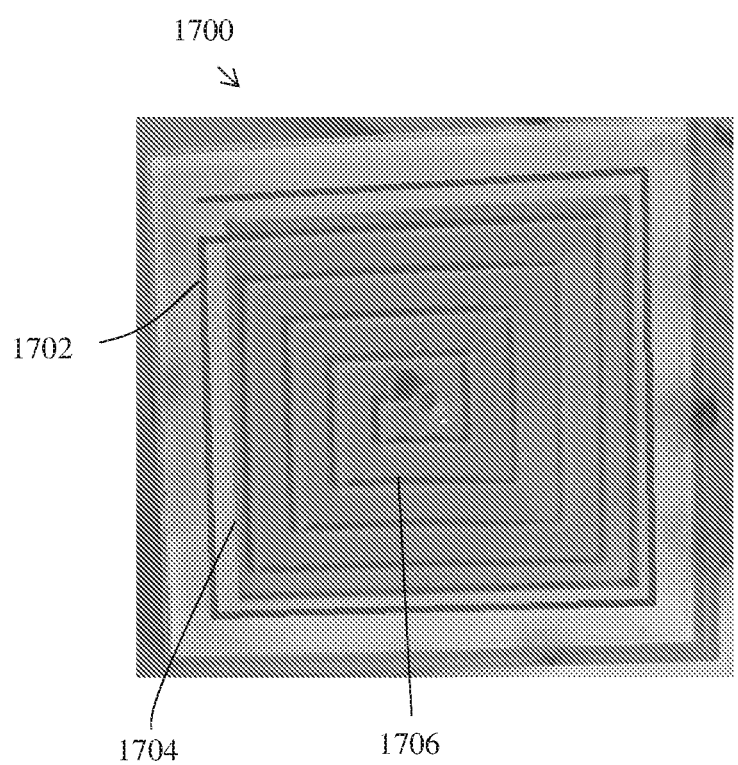
FIG. 17 illustrates an embodiment of adjusting a size of a filter membrane using an adhesive layer.

Because many applications require different amounts of volume of blood and buffer to function with the specific application, there is a need for the ability to design a filter with a variable amount of filter area. FIG. 17 shows an assembly 1700 whose spiral mini-channel 1706 extends beyond the adhesive cutout perimeter 1702. Furthermore, after compressing the adhesive against the output component's sealing surface, the pressure sensitive adhesive creeps into the channels and seals them completely or partially. Thus, the lines 1702 representing the adhesive cutout perimeter are covered by the double sided adhesive layer (shown in white) and are not being used because the adhesive has blocked that length of the channel. Therefore, in this design, the usable portion of the filter that is being used is defined by the double sided adhesive layer. The shaded portion 1704 is the area of the filter membrane that is being used for filtration of a blood sample. This sealing by the adhesive allows a designer to specify a cutout area for the application without the need to redesign the rigid housing. This benefit permits the use of the same manufactured rigid housing components to be adaptable to function with many different applications with different volume and dilution requirements. This capability eliminates the need to design new and expensive tooling to reconfigure the filter to a new size footprint. Instead, the adhesive layer is converted to the appropriate size for the application, which is much simpler and cheaper to implement than creating new molds for a different application.

As described above, typically sample processing includes using a precision pipette to collect a sample of blood from a vacutainer tube via venipuncture and depositing the sample into a centrifuge tube. A specific amount of buffer solution is then pipetted into the centrifuge tube with the blood sample. The mixture is then drawn into the pipette several times until it is homogeneous. The mixture is then centrifuged for a specified amount of time at high rotational speed. A specific amount of the supernatant is then pipetted onto the test strip. Using the devices and methods described herein, the volume of blood can be collected into a capillary, a swab, or pipetted. The device is agnostic to how the blood is collected. The blood can be mixed by swirling or stirring the mixture. The cells are separated from diluted plasma using a filter. The volume is deposited into the strip by counting drops or collecting a specified amount of sample.

The resources needed that are eliminated by the devices described herein are a precision pipette, a centrifuge, electrical power, and professional training, and cost. For many point-of-care applications, cell separation is a significant challenge that care providers face which the current devices and methods have solved using the filter assembly. Other products utilize tangential flow filtration and inertial focusing which are not as rapid or simple as the device described herein. In research, there is a lot of work in microfluidics to be able to automate all of these steps. However, a microfluidic device still requires electrical power, pressure pumps, specialized instrumentation, computer control, valves, professional training, and money. Furthermore, at micro-scales, processes like mixing become non-trivial since a small channel with a low Reynolds number does not facilitate turbulent mixing. Cell separation is also a very difficult task to perform in microfluidics. The ratio of blood to plasma is roughly 50%. Therefore, a filter would need to be very effective at separating cells from the plasma, which has not been properly demonstrated in the literature with high efficiency and low cost. Furthermore, a path to high volume manufacturing has not been demonstrated at this point for microfluidic cell separation.

The devices and methods described herein take advantage of the scales that are reasonable for high volume manufacturing. The devices and methods work in dimensions and scales that can have devices components injection molded to reduce the cost significantly. Because of this, a mixing task can easily be performed by stirring, swirling, inverting, or repeat pipetting. At this scale, the device can utilize use a large filter at the cost of collecting slightly more sample volume (1-2 drops). The pressure source in this device is derived from simple actions such as a squeezing action of a flexible container or depressing a micropipette plunger. All of the sample processing steps are intuitive and do not require significant training to perform correctly.

The filter design of the current application can have several advantages over currently available filter designs. In some such filter designs, the channels that receive filtrate from the filter may be disposed on a thin film or other flimsy material. Additionally, the channels may be formed by laser etching or otherwise removing material from the layer, causing it to become even more flimsy. The flimsiness of the layer comprising the channels requires the channels to be adequately spaced apart to allow for deflection or compression of the layer, which could cause obstruction of any channels spaced too close to one another. In contrast, the channels of the current design are provided on an inflexible or more rigid substrate that can be incapable of being bent. The rigidity of the substrate comprising the channels can allow for precise positioning of the channels. For example, the channels can be positioned very close to one another without concern for the channels becoming obstructed by deflection of the substrate. This capability can allow for a denser network of channels, providing faster and additional output capability of the filter.

Currently available filters can also provide a design in which a buffer solution is provided within the filter and is passively mixed at some point within the filtering process. Thus, the dilution of the sample is dependent upon the configuration and geometry of the filter design. In contrast, in the current design any buffer used is pre-mixed (e.g., in a flexible container) prior to applying the buffer and sample mixture to the filter. This pre-mixing allows the user to precisely select or calculate a desired dilution of the sample.

Currently available filters are not designed to accommodate the use of a wide variety of pressurization devices such as micropipettes, squeeze bottles, syringes, and bulb pipettes. These currently available devices are designed so that they can function with only a specific type of pressurization device. The current design is compatible with many pressurization devices with one design, which allows it to be used for a greater variety of applications.

Furthermore, many currently available filter designs lack a rigid substrate or housing providing stability to the filter. Such flexible designs are incapable of being easily placed on or attached (e.g., snapped) to a test cartridge. In contrast, the filter designs of the current application include rigid substrates or housings. Furthermore, these flexible designs will deform upon pressurization due to the lack of rigidity and cause unwanted ballooning of the assembly. The rigidity of the substrate or housing can allow it to be easily placed on or snapped onto a test cartridge and maintain its form under pressurization.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A sample filtration device comprising
    an input substrate comprising an inlet hole;
    a filter membrane in fluid communication with the inlet hole and configured to filter the sample into a filtrate;
    a double sided adhesive layer adhered to the filter membrane and the input substrate, the adhesive layer comprising a central cutout configured to expose a central portion of the filter membrane, wherein a size of an outer perimeter of the filter is smaller than a size of an outer perimeter of the adhesive layer; and
    an output substrate comprising one or more channels in fluid communication with the filtrate from the filter, the one or more channels in fluid communication with an outlet of the output substrate.

2. The sample filtration device of claim 1, wherein the filter membrane comprises an asymmetric filter membrane.

3. The sample filtration device of claim 1, wherein the filter membrane is adhered to the input substrate.

4. The sample filtration device of claim 1, wherein the filter membrane is adhered to the output substrate.

5. The sample filtration device of claim 1, wherein the sample fluid comprises whole blood.

6. The sample filtration device of claim 1, wherein the one or more channels comprises a serpentine channel or a plurality of channels.

7. The sample filtration device of claim 1, wherein the outlet comprises a spout.

8. The sample filtration device of claim 1, wherein a surface of at least one of the input substrate and output substrate adjacent to the filter membrane is flat.

9. The sample filtration device of claim 1, wherein the output substrate comprises a ridge around its perimeter.

10. The sample filtration device of claim 9, wherein the input substrate is sized to fit inside the ridge of the output substrate.

11. The sample filtration device of claim 1, wherein the input substrate comprises a ridge around its perimeter.

12. The sample filtration device of claim 11, wherein the output substrate is sized to fit inside a ridge of the input substrate.

13. The sample filtration device of claim 1, wherein the one or more channels extends throughout an area of the filter membrane.

14. The sample filtration device of claim 1, wherein the one or more channels comprise a spacing of about 1.5 mm between channels.

15. The sample filtration device of claim 1, wherein at least one of the input substrate and the output substrate comprises a rigid material.

16. The sample filtration device of claim 1, wherein a thickness of the double sided adhesive layer is greater than a thickness of the filter membrane.

17. The sample filtration device of claim 1, the double sided adhesive layer is configured to seal edges of the filter membrane.

18. The sample filtration device of claim 1, wherein the input substrate and filter membrane are adhered to a first side of the double sided adhesive layer and the output substrate is adhered to a second side of the double sided adhesive layer, the second side opposite to the first side.

19. The sample filtration device of claim 1, wherein the input substrate is adhered to a first side of the double sided adhesive layer and the filter membrane and output substrate are adhered to a second side of the double sided adhesive layer, the second side opposite to the first side.

20. A sample filtration device comprising
an input substrate comprising an inlet hole;
a filter membrane in fluid communication with the inlet hole and configured to filter the sample into a filtrate;
a double sided adhesive layer adhered to the filter membrane and the input substrate, the adhesive layer comprising a central cutout configured to expose a central portion of the filter membrane, wherein a size of an outer perimeter of the filter is smaller than a size of an outer perimeter of the adhesive layer; and
an output substrate comprising one or more channels in fluid communication with the filtrate from the filter, the one or more channels in fluid communication with an outlet of the output substrate, wherein the double sided adhesive layer is adhered to the output substrate.

* * * * *

UNITED STATES PATENT AND TRADEMARK OFFICE
CERTIFICATE OF CORRECTION

PATENT NO. : 11,946,843 B2  
APPLICATION NO. : 16/625799  
DATED : April 2, 2024  
INVENTOR(S) : Estevan Mendoza Page 1 of 1

It is certified that error appears in the above-identified patent and that said Letters Patent is hereby corrected as shown below:

On the Title Page

At Item (73) Assignee: please delete "SPLITRX LLC, Los Gatos, CA (US)" and insert --CanaryQ, Inc., Mountain View, CA (US)--

Signed and Sealed this
Seventeenth Day of December, 2024

Derrick Brent
*Acting Director of the United States Patent and Trademark Office*